US008802931B2

(12) United States Patent
Pick et al.

(10) Patent No.: US 8,802,931 B2

(45) Date of Patent: Aug. 12, 2014

(54) SALT RESISTANT TRANSGENIC PLANTS

(75) Inventors: Uri Pick, Nes Ziona (IL); Orna Livneh, Rehovot (IL); Eli Khayat, Western Galilee (IL); Rina Walther, Rosh Hanikra (IL); Avi Gabai, Vardon (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 1036 days.

(21) Appl. No.: 11/574,506

(22) PCT Filed: Sep. 1, 2005

(86) PCT No.: PCT/IL2005/000932

§ 371 (c)(1), (2), (4) Date: Jul. 6, 2007

(87) PCT Pub. No.: WO2006/025059

PCT Pub. Date: Sep. 3, 2006

(65) Prior Publication Data

US 2009/0044290 A1 Feb. 12, 2009

Related U.S. Application Data

(60) Provisional application No. 60/606,415, filed on Sep. 2, 2004.

(51) Int. Cl.

| | |
|---|---|
| ***C12N 15/05*** | (2006.01) |
| ***C12N 15/01*** | (2006.01) |
| ***C12N 15/11*** | (2006.01) |
| ***C12N 15/63*** | (2006.01) |
| ***C12N 15/82*** | (2006.01) |
| ***C12N 1/12*** | (2006.01) |
| *C07H 21/04* | (2006.01) |
| *C07K 14/405* | (2006.01) |
| *C12N 15/52* | (2006.01) |

(52) U.S. Cl.

USPC ..... 800/298; 800/278; 800/317.2; 800/317.3; 435/410; 435/414; 435/417; 435/420; 435/425; 435/429; 435/430; 435/422; 435/419; 435/320.1

(58) Field of Classification Search

None

See application file for complete search history.

(56) References Cited

U.S. PATENT DOCUMENTS

| | | | | |
|---|---|---|---|---|
| 5,650,307 | A * | 7/1997 | Sijmons et al. | 435/69.6 |
| 2002/0178464 | A1 | 11/2002 | Gaxiola et al. | |
| 2004/0040054 | A1 | 2/2004 | Silva et al. | |
| 2005/0108791 | A1 * | 5/2005 | Edgerton | 800/284 |

FOREIGN PATENT DOCUMENTS

| | | |
|---|---|---|
| WO | WO 91/06651 | 5/1991 |
| WO | WO 03/031631 | 4/2003 |
| WO | WO 2006/025059 | 3/2006 |

OTHER PUBLICATIONS

Gonzalez-Ballester et al. (NCBI, GenBank Sequence Accession No. AY058213, Published Jun. 1, 2002).*

Gaxiola et al. (PNAS, 98:11444-11449, 2001).*

Weiss et al. (Plant Physiol., 112:1693-1702, 1996).*

Dewitt et al. (Plant Physiol., 112:833-844, 1996).*

Arango et al. (Planta, 216:355-365, 2003).*

Wolf et al. (Plant Molecular Biology, 28:657-666, 1995).*

Wells (Biochemistry 29:8509-8517, 1990).*

Ngo et al., (The Protein Folding Problem and Tertiary Structure Prediction, K. Merz., and S. Le Grand (eds.) pp. 492-495,1994.*

Keskin et al. (Protein Science, 13:1043-1055, 2004).*

Thornton et al. (Nature structural Biology, structural genomics supplement, Nov. 2000).*

Guo et al. (PNAS, 101: 9205-9210, 2004).*

Blumwald et al. Sodium transport in plant cells. Biochemica et Biophysica Acta. 2000. 1465: 140-151.*

Axelsen et al. Evolution of substrate specificities in the P-type ATPase Superfamily. 1998. 46: 84-101.*

Ajalov et al., "The Adaptation of *Dunaliella salina* Cells to High Salt Concentration, Isolation of 63 and 28 KDA Salt-Induced Polypeptides", *Biochemical Society Transactions*, 24(4):5345 (1996).

Apse et al., "Salt Tolerance Conferred by Overexpression of a Vacuolar Na+/H+ Antiport in *Arabidopsis", Science*, 285:1256-1258 (Aug. 20, 1999).

Arango et al., "The plasma membrane proton pump ATPase: the significance of gene subfamilies", *Planta*, 216:355-365 (2003).

Dewitt et al., "Targeting of Two *Arabidopsis* H+-ATPase Isoforms to the Plasma Membrane", *Plant Physiology*, 112:833-844 (1996).

Gaxiola et al., "Drought- and salt-tolerant plants result from overexpression of the AVP1 H+-pump", *PNAS*, 98:11444-11449 (2001).

(Continued)

*Primary Examiner* — Brent T Page

*Assistant Examiner* — Ashley K Buran

(57) ABSTRACT

The present invention provides transgenic plants transformed with exogenous nucleic acid encoding a *Dunaliella* plasma membrane (PM)-ATPase. The transgenic plant has increased tolerance to salt as compared to a corresponding non-transgenic plant. The present invention also provides nucleic acids encoding a chimeric PM-ATPase, which comprise a first portion encoding a plant PM-ATPase or a fragment thereof, and a second portion encoding a *Dunaliella* PM-ATPase or a fragment thereof. The present invention also discloses a method of producing a transgenic plant having an increased tolerance to salt as compared to a corresponding non-transgenic plant, a method of modifying a plant capacity to survive salt shock, and a method of modifying plant recovery after exposure to salt stress, by introducing into one or more cells of a plant an exogenous nucleic acid encoding a *Dunaliella* PM-ATPase. Also provided by the present invention are plant cells comprising an exogenous nucleic acid encoding a *Dunaliella* PM-ATPase, and plant seeds and progeny obtained from the transgenic plants.

17 Claims, 21 Drawing Sheets

(56) References Cited

OTHER PUBLICATIONS

Goff et al., "A Draft Sequence of the Rice Genome (*Oryza sativa* L. ssp. japonica)", *Science*, 296:92-100 (Apr. 5, 2002).
Gong et al., "Genes That Are Uniquely Stress Regulated in Salt Overly Sensitive (sos) Mutants", *Plant Physiology*, 126:363-375 (May 2001).
International Preliminary Report on Patentability for PCT/IL2005/000932 dated Aug. 21, 2007 (7 sheets).
International Search Report for PCT/IL2005/000932 dated Jul. 13, 2007 (7 sheets).
Kalampanayil et al., "Identification and characterization of a salt-stress-induced plasma membrane H+-ATPase in tomato", *Plant, Cell, and Environment*, 24:999-1005 (2001).
Kawasaki et al., "Gene Expression Profiles During the Initial Phase of Salt Stress in Rice", *The Plant Cell*, 13:889-905 (Apr. 2001).
Kerkeb et al., "Plasma membrane H+-ATPase activity is involved in adaptation of tomato calli to NaCl", *Physiologia Plantarum*, 111:483-490 (2001).
Kreps et al., "Transcriptome Changes for *Arabidopsis* in Response to Salt, Osmotic, and Cold Stress", *Plant Physiology*, 130:2129-2141 (Dec. 2002).
Niu et al., "Ion Homeostasis in NaCl Stress Environments", *Plant Physiology*, 109:735-742 (1995).
Palmgren, M. G., "Plant Plasma Membrane H+-ATPases: Powerhouses for Nutrient Uptake", *Ann Rev Plant Physiol Plant Mol Biol*, 52:817-845 (2001).
Pick et al., "Adaptation of the halotolerant alga *Dunaliella* to high salinity", In A Lauchili, U Luthge, eds, Salinity: Enviroment-Plants Molecules, Ed Acad. Pub. Dordrecht. Kluwer, pp. 97-112 {2002).
Reuveni et al., "Modification of Proton Transport Kinetics of the Plasma Membrane H+-ATPase after Adaptation of Tobacco Cells to NaCl", *J. Plant Physiol.*, 142:312-318 (1993).
Seki et al., "Monitoring the expression profiles of 7000 *Arabidopsis* genes under drought, cold and high-salinity stresses using a full-lenth cDNA microarray", *The Plant Journal*, 31(3):279-292 (2002).
Sekler et al., "Purification and Properties of a Plasma Membrane H+-ATPase from the Extremely Acidophilic Alga *Dunaliella acidophila", Plant Physiology*, 101:1055-1061 (1993).
Shi et al., "Overexpression of a plasma membrane Na+/H+ antiporter gene improves salt tolerance in *Arabidopsis thaliana", Nature Biotechnology*, 21:81-85 (Jan. 2003).
Vitart et al., "Evidence for a role in growth and salt resistance of a plasma membrane H+-ATPase in the root endodermis", *The Plant Journal*, 27:191-201 (2001).
Weiss et al., "Primary Structure and Effect of pH on the Expression of the Plasma Membrane H+-ATPAse from *Dunaliella acidophila* and *Dunaliella salina", Plant Physiology*, 112:1693-1702 (1996).
Wolf et al., "Primary structure of the plasma membrane H+-ATPase from the halotolerant alga *Dunaliella bioculata", Plant Molecular Biology*, 28:657-666 (1995).
Written Opinion of the International Searching Authority for PCT/IL2005/000932 dated Jul. 13, 2007 (6 sheets).
Yu et al., "A Draft Sequence of the Rice Genome (*Oryza sativa* L. ssp. indica)", *Science*, 296:79-91 (Apr. 5, 2002).
Zhang et al., "Expression of the plasma membrane H+-ATPase gene in response to salt stress in a rice salt-tolerant mutant and its original variety", *Theor Apll Genet*, 99:1006-1011 (1999).
Zhang et al., "Transgenic salt-tolerant tomato plants accumulate salt in foliage but not in fruit", *Nature Biotechnology*, 19:765-768 (Aug. 2001).

* cited by examiner

```
175                                AGGATG AGTGGAAAGG AGAGGACCGA
201   GGAAAATGGG GCCGTCAAGC AGGACACGAA GGAGCAGGTC AAGAAATCGG
251   CCGACAATGG AGATAAAGGC GTGGACGAGG TGGACTTCGC CAAGATTGGG
301   CTGGAGGATG CCTTCAAGTA CCTGAATTGC TCCGAGCATG GTCTGAGCGG
351   CGCTGAAGCC GAAGCACGGC TTAAACAGCA CGGGCCTAAT AAGCTCCCTG
401   ACAACTCCCG TAACCCAGTT CTGGTGTACT TTGGGTACAT GTGGAACCCC
451   TTGGCTTGGG CCATGGAGGC GGCTGCTATC ATTGCCATTG CTTTGGTGGA
501   TGGTGCAGAC TTCGCGCTGA TTGTGGGCCT GCTGATCATC AATGCCACTA
551   TCAGTTTCGT CGAGGAGAGC AATGCTGATA AGGCTATCAA GGCCTTGTCA
601   GCTGCCCTAG CACCCAAGGC CATGGCCTTA CGAAATGGAG CCATGGTGAC
651   CATAGACGCG GTGGACCTTG TGCCCGGGGA TGTGATTTTG ATTCGGATCG
701   GTAACGTTGT GCCCGCCGAT GTTAAATTGC TTCCGGAACA TGGCGCGGAT
751   GACTATGAGA CGCCCGTGCA GATTGACCAA GCTGCCTTGA CAGGAGAGTC
801   CTTACCAGCC AAGAAGTTCA CAGGCAACGT GGCCTTCAGC GGTTCTACTG
851   TCAAACAAGG AGAGCGACAC GCTGTTGTGT ATGCCACCGG CGTGAACACC
901   TTCTTTGGCC GTGCTGCTGC GCTCATCAGT GGGACTCACA ACGTAGCAAA
951   TATTCAGCGT GTCATGAACA GGATCGGTGG CCTTTGTCTC ATCACCATTG
1001  GAGTATGGGT CGTCATTGAA GTGCCTGTGC AGTTTGCACA TTATAAGCAT
1051  TCATGCGTAG CTGGCAAAGA GGGCTGCCCC ACCCTACTCA ACATGCTGGT
1101  TATACTGGTG GGTGCTATTC CCATCGCCAT GCCCACTGTG CTGTCAGTGA
1151  CCTTGGCCCT GGGAGCTTAC AAGCTTGCAC GTGAAGGCGC TATTGTGACT
1201  CGGATGAGTG CTGTGGAAGA GATGGCAGGC TTGGATGTGT TATGCTCTGA
1251  CAAGACTGGA ACCTTGACCC TTAACAAGCT ATCAATCGAT CCTAGCAATG
1301  TGTTCCCTGT GGGCACGATG GACATCCCAG AGGTTATGAA GTTCGGCGCT
1351  TTGTCTGCCA ACATAATCAC TGAGGAGCCT ATCGATATGG TGCTGTGGGA
1401  GTCATACCCT GAGCGGGAGA AATTAAAATC AGAGTACAAG CACACCAAGT
1451  ACTTCCCATT CAACCCCAAT GACAAGATCA CCATCGCAAC CGTCCTTGAG
1501  ATTGCCACTG GCCGCGTGTT CCGAGTCCTC AAAGGCTCCC CTCAGGTGGT
```

FIGURE 2(i)

```
1551 CTTGGCCAAG GCATGGAATG CGCAAGCCCT GGATGGGCCT GTGAATGAAA
1601 AGATAAAAGA GTATGCAGGC AGAGGCTTCC GTTCTCTGGG CATTGCCATG
1651 GCAGAGGGGG ATGGCAAGGA CGGAACAAAG TGGGAGATGC TGGCGGTGCT
1701 GCCCATGTTT GACCCCCCTC GCCACGACAC CAAGGAAACC ATTGAGCGCT
1751 GCATGAAGCA GGGTATTGCA GTCAAGATGG TCACAGGCGA CCACTTGCTG
1801 ATTGGTAAAG AGACTGCCAA GATGCTGGGC ATGGGTACTG AGATGTACCC
1851 CAGTGAGGTG CTGATCAAGG CCCGCAATGG TGATGTGGAG GCGCCGCATG
1901 GTTACAAAAA CTACGTGGCA ATGGTGGAGG CATGCAACGG CTTTGCACAG
1951 GTCTTCCCTG AACACAAGTT TGAAATTGTC GAAATCCTGC AAGAAGCCCA
2001 CCACCGTGTT GGCATGACAG GTGACGGTGT GAACGACGCG CCTGCGCTCA
2051 AGAAGGCGCA TGTAGGTGTG GCTGTGGCAG ATGCCACAGA TGCCGCCCGA
2101 GGTGCCGCTG ACATCGTGCT CACCGAGCCT GGTCTATCAA CCATTGTGAC
2151 CGCTGTCATT GGCGCACGCA AGATCTTCAA GCGCATGACC ACTTATGCCA
2201 AGTACACCAT TTCCGTGACC TTCCGTATCG CCTTTACCTT CGGCCTCCTC
2251 ACTGTCATCT ACGACTGGTA CTTCCCCACC ATCCTCATCG TCATCTTGGC
2301 TGTCTTTAAT GATGGTGCCA TGATCGCCCT ATCCAAGGAC CGTGTGGTGG
2351 CCTCTGTGTT GCCTAGCACC TGGAACCTCG CCACCATCTT CGTACCGGGT
2401 TTTGTCTACG CAATGTGGCT GACTCTCTCC TCCTGGGCAC TGTACCAGGT
2451 GGCCACACAT AGCACCTTCT TTGAACGCAT GACCCCACTG CCATCACTGA
2501 ACACCCAGCA TGCGACTCTC ATATCCTGGT GTGAGGATGA GATCAGCAGC
2551 AAGTTGGGCG TCAATCCTCA AGATTCCCTG TGCACGTATC CAAGCTATGC
2601 TGATCAGCTG AATGAATGCA AAGGCTCTGT GAGCCTGAGC TCACAGGTCC
2651 CTGGCGTGCC CACCATTTTG GATCAGTGCG TAACTGAGCA GCGCTACATT
2701 CGAGATGCCT TGACACGTGC CCTCATTTAC ACCCACCTCT CTGTCTCTGG
2751 CCAAGCCGTT GTGTTTGTGG TGCGCACGTC CGGCTTCTCT CTGAAGGAAG
2801 TGGCAGGCGT CTCCACCTAT GTCGCTTTCG CTCTTGCCCA GTTTGGTGCC
```

FIGURE 2(ii)

```
2851  ACAATGTTTG GCATCTTTGG CCTGGGAGGC TATAACAAGC CCCGACAGAA
2901  TTTTGACAAC TGCCAGTTCT GTGATTACTC CACCCATAAT CGCGTGCTGT
2951  TCTTTAACTC AGAGGTGGAA CCTCGCGCTG GTACAGAATC TGTCTACACT
3001  GCTTCTGTCA TTGGATGCGG AGGTTATGTC ATTGTCGCTT GGATCTGGGC
3051  TGCTCTGTTC TACACTGCGC TGGATCCCTT GAAGTGGGGC TTGATGTGGA
3101  TCATGAACGA TGATGGCTTC AGGGACCGGC ACGCCTGGCG CAAGTCCAAC
3151  CACGAGGCCA TGGAGCGCCG TAGCAGGGAG CAGTTGGACA ACAAAGAGTT
3201  CGCTGGCCCC TCAGGCATGG TGCCTGCCAA CTTCTCTAAC CCTCTTGGCC
3251  GTGCCTCCAT GTCCAAGCCC GTGTCCGCTT TGCTTGACCG AAAGTCTGCA
3301  TCCCTTGTGG CTATTAACCG CAGCTCCATG ACTGTCAGTC ACGACCCCAA
3351  CCATGCACTG AACATCGGAC GCCGCTCCAT GATTGGACGC CCCTCTGGTC
3401  CTTTGGGACG CAACTCCAAC ACGGGTCAAA GCAACCCCCT GAACAGCTCT
3451  TCAGTGGAGA TCAAGCCCGA TGCGCCCAAC AAGGTGTAAG AAAACCCATC
3501  AGTGAGATGT AAGGCAAACT ACTGTGCAAG AGGCGATGTC GGTACATGCG
3551  CTCGTGTGTC TGTGTAGGAA GGTCGTGCGA GTGCCCTATG TCATGGGCCC
3601  TATTTCAATG TTTTCTATGT ACAAGAACTT GAGTGGTA
```

FIGURE 2(iii)

```
175                                   AGGATG AGTGGAAAGG AGAGGACCGA
201  GGAAAATGGG GCCGTCAAGC AGGACACGAA GGAGCAGGTC AAGAAATCGG
251  CCGACAATGG AGATAAAGGC GTGGACGAGG TGGACTTCGC CAAGATTGGG
301  CTGGAGGATG CCTTCAAGTA CCTGAATTGC TCCGAGCATG GTCTGAGCGG
351  CGCTGAAGCC GAAGCACGGC TTAAACAGCA CGGGCCTAAT AAGCTCCCTG
401  ACAACTCCCG TAACCCAGTT CTGGTGTACT TTGGGTACAT GTGGAACCCC
451  TTGGCTTGGG CCATGGAGGC GGCTGCTATC ATTGCCATTG CTTTGGTGGA
501  TGGTGCAGAC TTCGCGCTGA TTGTGGGCCT GCTGATCATC AATGCCACTA
551  TCAGTTTCGT CGAGGAGAGC AATGCTGATA AGGCTATCAA GGCCTTGTCA
601  GCTGCCCTAG CACCCAAGGC CATGGCCTTA CGAAATGGAG CCATGGTGAC
651  CATAGACGCG GTGGACCTTG TGCCCGGGGA TGTGATTTTG ATTCGGATCG
701  GTAACGTTGT GCCCGCCGAT GTTAAATTGC TTCCGGAACA TGGCGCGGAT
751  GACTATGAGA CGCCCGTGCA GATTGACCAA GCTGCCTTGA CAGGAGAGTC
801  CTTACCAGCC AAGAAGTTCA CAGGCAACGT GGCCTTCAGC GGTTCTACTG
851  TCAAACAAGG AGAGCGACAC GCTGTTGTGT ATGCCACCGG CGTGAACACC
901  TTCTTTGGCC GTGCTGCTGC GCTCATCAGT GGGACTCACA ACGTAGCAAA
951  TATTCAGCGT GTCATGAACA GGATCGGTGG CCTTTGTCTC ATCACCATTG
1001  GAGTATGGGT CGTCATTGAA GTGCCTGTGC AGTTTGCACA TTATAAGCAT
1051  TCATGCGTAG CTGGCAAAGA GGGCTGCCCC ACCCTACTCA ACATGCTGGT
1101  TATACTGGTG GGTGCTATTC CCATCGCCAT GCCCACTGTG CTGTCAGTGA
1151  CCTTGGCCCT GGGAGCTTAC AAGCTTGCAC GTGAAGGCGC TATTGTGACT
1201  CGGATGAGTG CTGTGGAAGA GATGGCAGGC TTGGATGTGT TATGCTCTGA
1251  CAAGACTGGA ACCTTGACCC TTAACAAGCT ATCAATCGAT CCTAGCAATG
1301  TGTTCCCTGT GGGCACGATG GACATCCCAG AGGTTATGAA GTTCGGCGCT
1351  TTGTCTGCCA ACATAATCAC TGAGGAGCCT ATCGATATGG TGCTGTGGGA
1401  GTCATACCCT GAGCGGGAGA AATTAAAATC AGAGTACAAG CACACCAAGT
1451  ACTTCCCATT CAACCCCAAT GACAAGATCA CCATCGCAAC CGTCCTTGAG
1501  ATTGCCACTG GCCGCGTGTT CCGAGTCCTC AAAGGCTCCC CTCAGGTGGT
1551  CTTGGCCAAG GCATGGAATG CGCAAGCCCT GGATGGGCCT GTGAATGAAA
1601  AGATAAAAGA GTATGCAGGC AGAGGCTTCC GTTCTCTGGG CATTGCCATG
```

FIGURE 3(i)

```
1651  GCAGAGGGGG ATGGCAAGGA CGGAACAAAG TGGGAGATGC TGGCGGTGCT
1701  GCCCATGTTT GACCCCCCTC GCCACGACAC CAAGGAAACC ATTGAGCGCT
1751  GCATGAAGCA GGGTATTGCA GTCAAGATGG TCACAGGCGA CCACTTGCTG
1801  ATTGGTAAAG AGACTGCCAA GATGCTGGGC ATGGGTACTG AGATGTACCC
1851  CAGTGAGGTG CTGATCAAGG CCCGCAATGG TGATGTGGAG GCGCCGCATG
1901  GTTACAAAAA CTACGTGGCA ATGGTGGAGG CATGCAACGG CTTTGCACAG
1951  GTCTTCCCTG AACACAAGTT TGAAATTGTC GAAATCCTGC AAGAAGCCCA
2001  CCACCGTGTT GGCATGACAG GTGACGGTGT GAACGACGCG CCTGCGCTCA
2051  AGAAGGCGCA TGTAGGTGTG GCTGTGGCAG ATGCCACAGA TGCCGCCCGA
2101  GGTGCCGCTG ACATCGTGCT CACCGAGCCT GGTCTATCAA CCATTGTGAC
2151  CGCTGTCATT GGCGCACGCA AGATCTTCAA GCGCATGACC ACTTATGCCA
2201  AGTACACCAT TTCCGTGACC TTCCGTATCG CCTTTACCTT CGGCCTCCTC
2251  ACTGTCATCT ACGACTGGTA CTTCCCCACC ATCCTCATCG TCATCTTGGC
2301  TGTCTTTAAT GATGGTGCCA TGATCGCCCT ATCCAAGGAC CGTGTGGTGG
2351  CCTCTGTGTT GCCTAGCACC TGGAACCTCG CCACCATCTT CGTACCGGGT
2401  TTTGTCTACG CAATGTGGCT GACTCTCTCC TCCTGGGCAC TGTACCAGGT
2451  GGCCACACAT AGCACCTTCT TTGAACGCAT GACCCCACTG CCATCACTGA
2501  ACACCCAGCA TGCGACTCTC ATATCCTGGT GTGAGGATGA GATCAGCAGC
2551  AAGTTGGGCG TCAATCCTCA AGATTCCCTG TGCACGTATC CAAGCTATGC
2601  TGATCAGCTG AATGAATGCA AAGGCTCTGT GAGCCTGAGC TCACAGGTCC
2651  CTGGCGTGCC CACCATTTTG GATCAGTGCG TAACTGAGCA GCGCTACATT
2701  CGAGATGCCT TGACACGTGC CCTCATTTAC ACCCACCTCT CTGTCTCTGG
2751  CCAAGCCGTT GTGTTTGTGG TGCGCACGTC CGGCTTCTCT CTGAAGGAAG
2801  TGGCAGGCGT CTCCACCTAT GTCGCTTTCG CTCTTGCCCA GTTTGGTGCC
2851  ACAATGTTTG GCATCTTTGG CCTGGGAGGC TATAACAAGC CCCGACAGAA
2901  TTTTGACAAC TGCCAGTTCT GTGATTACTC CACCCATAAT CGCGTGCTGT
2951  TCTTTAACTC AGAGGTGGAA CCTCGCGCTG GTACAGAATC TGTCTACACT
3001  GCTTCTGTCA TTGGATGCGG AGGTTATGTC ATTGTCGCTT GGATCTGGGC
3051  TGCTCTGTTC TACACTGCGC TGGATCCCTT GAAGTGGGGC TTGATGTGGA
3101  TCATGAACGA TGATGGCTTC
```

FIGURE 3(ii)

FIGURE 4A
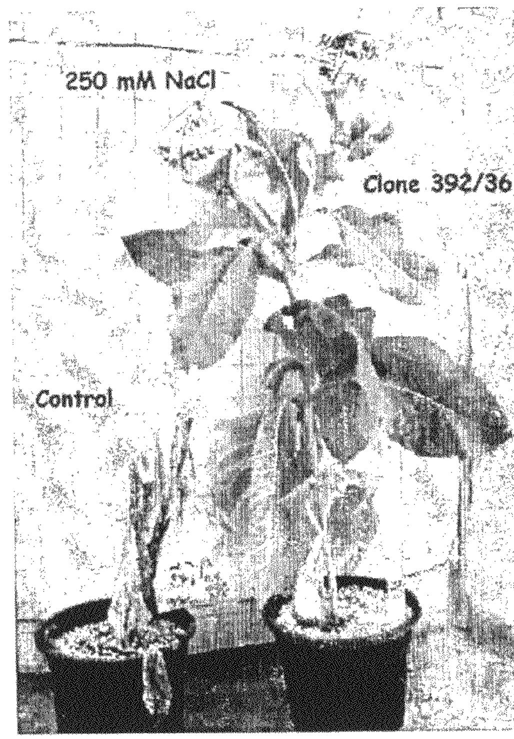
FIGURE 4B
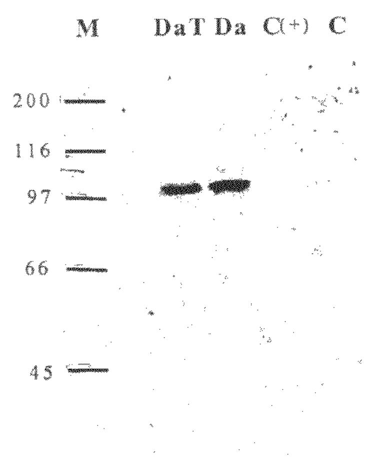
FIGURE 5

```
1    TGCAGGATTC GGCACGAGGG AGTGGTGGGC TTGCTTCCTG GCTCCAGAGT
51   AGTTCCGCAC CTGTTCACGA GCAAATGGCG CACCTGTGAG GCCCGCTGCG
101  TGCAAGTGCG CCTTCTTCGC GCCACACTCC CACCTTTGAC ACGCAGACAC
151  AGAGCGCCCT GACCTGTCAG AGCTTGCTTT AGGCCGTGAG CTGCCAACCG
201  ACTCAGCCGT CTCTGCCTGG AGAGGGCCCC TGGGCCCGCT GAGTGCCGCA
251  ACATGGCGGA CATCAAGGAA GGAGTCGAGG AAGGATCGGT GAAGGTGGAC
301  ATGATCAAGG AGCCCCTCAC ACAAGGGGAC ACTGGCGTGG ATGAGGTGGA
351  CTTTGCCAAG ATTACTCTGG ACGATGCCTT CAAGTACTTG AATTGCAACA
401  AGCACGGGCT CAGCAGTGCC GAAGCAGCTG CTCGTCTTCA ACAGCACGGG
451  CCCAACAAGC TTCCTGACAG TTCACGCAAC CCTGTCCTTG TCTTCCTTGG
501  ATACATGTGG AACCCCCTGG CGTGGGCCAT GGAGGCAGCC GCAATCATCT
551  CCATTGCCCT CCTGGATGTG GCAGATTTCG TGCTCATTGT GGGCTTGCTG
601  CTCATCAATG CCATTATCAG TTTCTATGAG GAGAGCAACG CCGACAAGGC
651  CATCAAGGCC TTGACAGCTG CCCTTGCACC CAAGGCCATG GTCGTGCGAG
701  ATGGTGCCAT TGTGACCATC GATGCTGTGA ATCTCGTGCC GGGGGACGTC
751  ATCTTAATCC GCTTGGGCAA CATCGTACCA GCAGACGTCA AGCTGCTGGA
801  AGAAGAGGGA GCTGATGAGG GGGAGCAGGA AGCGCCCATG CAGATCGACC
851  AAGCCGCCCT CACAGGAGAG TCCCTTCCGG CCAAGAAGTT CACGGGCGAC
901  GTGGCCTTCA GCGGCTCGAG CATCAAGCAG GGAGAGCGCC ATGCAGTGGT
951  GTATGCTACT GGTGTGAACA CCTTCTTCGG ACGTGCAGCT GCCCTCATCA
1001 GCGGCACCAA CAACGTATCC AACCTGCAGA CTGTCATGAA CAAGATGAGC
1051 GCCATCTGCA TCGTCACCAT CCTGCTGTGG GTCGTTGTCG AGCTGGCCGT
1101 GCAATTTGGG CACTACTCGC ATGAATGCGT TGGTGGCAGA GAGGGCTGCC
1151 CCACCCTGCT GAATATGCTG GTGGTGCTGG TGGGCGGTAT TCCCATTGCC
1201 ATGCCCACTG TGCTGTCCGT GACCCTCGCC CTGGGTGCCT ACAAGCTTGC
1251 ACGCGAGGGT GCCATCGTCA CCCGTATGAG CGCCGTAGAG GAGATGGCAG
1301 GCATGGATGT GCTGTGCTCT GACAAAACCG GCACCCTCAC CTTGAACAAG
1351 CTGTCCATTG ACAAGAGCAT GGTGGTGCCG GTGGGCAACA TGGGCGTGGA
1401 TGAGATCATG AGAATGGGCG GCCTGTCTGC CATTACAGTC ACAGAGGAGC
1451 CCATCGATAT GGTGCTGTGG GAGTCTTATC CAGACAGGGA AACAATTAAG
```

FIGURE 6(i)

```
1501  AGGGACTACA AGCACACCAA GTACTTCCCC TTCATCCCCA ATGACAAGAT
1551  TACCATCGCA ACGTGCCTGG AGATCGCCAC CGGTAGGGTG TTCCGCGTGC
1601  TGAAGGGCTC TCCTCAGGTG GTGCTGGCCA AGGCGTGGAA TGCAGCCGAG
1651  CTGGATGCCA CCGTGAACCA GAAGATGGTG GAATTTGCAA ACCGCGGCTT
1701  CCGCGCGCTG GGCTTGGCTA TGGCAGACGG CGACGGCAAA GATGGCACCA
1751  AGTGGGAGAT GCTGGCGCTG CTGCCGCTGT TTGACCCCCC TCGCCACGAC
1801  ACCAAGGAGA CCATCGAGCA CTGCCAGAAC CAGGGCATCC AAGTCAAGAT
1851  GATCACTGGT GACCACTTGC TTATCGGGAA GGAAACCGCC AAGATGCTGG
1901  GCATGGGCAC TGAGATGTTC CCCAGTGAGG TCATGATCAA GGCCCGCAAT
1951  GGCGACGCAA GCCAGCTGCA CGGCTACAAG AACTTTGTGG AGATGGTGGA
2001  GACCTGCAAC GGCTTTGCCC AGGTGTTCCC GGAGCACAAG TTTGAGATCG
2051  TCAAGATCCT GCAGGACTCC AACCACGTCG TCGGCATGAC AGGTGATGGT
2101  GTGAATGACG CACCCGCCCT GAAGAAGGCT GACGTGGGTG TGGCTGTGGC
2151  TGACGCCACC GATGCTGCTC GTGGTGCTGC CGACATCGTG CTGACGGAGC
2201  CTGGCTTGTC CACCATCGTG ACGGCGGTGA TCGGCGCGCG CAAGATCTTC
2251  CAGCGCATGA CCACCTACTC CAAGTACACC ATCGCCATGA CCTTCCGTAT
2301  CTGCTTCACC TTTGGGCTGA TCACCGTCAT CTACGACTGG TACTTCCCCA
2351  CCATCCTCAT CGTCATCATG GGTGTCTTCA ACGATGGTGC CATGATTGCG
2401  CTGTCTAAGG ACCGTGTGGT GGCCTCCAAG ACGCCCAATA GCTGGAACAT
2451  CACCAACATC TTCATCATGG GCATGGTGTA CGGCCTGTAC CTCACCCTCT
2501  CCACATGGGC CTTGTACCAG ACTGCCACCA AGACCACGTT CTTCGAGGAC
2551  AAGACACCCT TGCATTCACT CAATGACCAG TACAGCGTCC TGCAGCCCTG
2601  GTGTGAGGAC GAAGTGCGGG CCAAGCTTGG ACAAACCATC GACCCCTACG
2651  CCTCACTGTG CGAGTCCAAC AGCTACGCCA AGCAGTTTGA CGAGTGCGAG
2701  GGATACCAGA AGGGCTCAGG CGTGCAGGTG GAGGACGTCC CTACCCTGCA
2751  TGCCCAATGC GTGACTGAGC AACGTTACCT GCGTGGCGCC ATGACGCGCT
2801  CCCTCATCTA CACCCAGGTC TCAATTTCTG GTCAGGCCCT CGTGTTTGTC
2851  GTCCGTACTG CGGGCTACTC CTTGATGGAG CGCGCGGGCA CCTCCACATA
2901  CCTGGCCTTC TTCTTTGCCC AGGTGGGCGC CACGCTGTTT GGTATCTTTG
2951  GCCTGGGTGG CTTTGAGAAG CCCCGCCACC AGCTGGAGGA CTGCCAGTTC
```

FIGURE 6(ii)

```
3001  TGCGACTACT CCTTCCATGA GCCCGTAGAC TGGTTTGACT CCGGGATTGT
3051  GCCTGAGTCC GGCACAGAGT CCGACTTCAC TGCCTCTGTC ATCGGATGCG
3101  GTGGTTACGT GATTGTGGCC TGGATCTGGT CTGCCATTTG GTACGTGCTG
3151  CTGGACCCCA TCAAGTGGAT CCTGTTCTGG ATCTTGAACG AGGAGGGCTT
3201  CAGGGACACG ATGTCCTGGC GCGAGAGCAC CAAGAGGAGC CTGGACCGCC
3251  GCAGCAAGGA TGACATCGGC GACAAGGAGT TCACGGGGCC CTCTGGCATG
3301  GTGCCGGCCA ACTACTCCAA CCCCCTGGGC CGTGCGTCCA TGTCCAAGCC
3351  TGTGTCAGCT GTGCTGGACC GCAAGTCCGC CTCCCTGGTT GCTATCAACC
3401  GCAACTCTAT GACTGTGAGC CAGGACCCCA ACCGCGCGCT CAACATCGGC
3451  CGGCGCTCCA TGATTGGCCG CCCCTCTGGG CCTGTTGGCC GCACGTCCAT
3501  GCCCTTGGGC CGTATCTCGC GCACTTCCAA CACCTTGTCC ACAGGCTCTA
3551  AGGATGGCCA GATCGGCAGA GGAAgCAAGC CTCTGAACAG CTCGTCCGCT
3601  GAGATCAAGC CCGACAAGTA TGACTTCGCT TCCACCATCA GGGAGTGAGC
3651  CCTCTCTCTC TCGTCAGCAA GCTGTCAAAA GCTGTTGAGA GTGATTGGGT
3701  GACCCCCATG AATGGATAAT GGAGAGTGCA TGTGAAACCT TTGGTTCCAG
3751  CAAGCAGGGG CAGAACACCC TTGCCTTAGT TCGAACAAAC TGGCCATCAG
3801  GGTTGATCCT CCTGTGCAGG TAGAGGGCGC GTCCTTCAGC GCTCCACTCC
3851  TTGTCTGAGT GCACATACGT GCGTGCCTGC ACCTGTTCTC ACCCATTCTC
3901  CCTCATTGTT GCAATGTGGA AGTATTGCTG TGCTCATATG ATGATTCACT
3951  TTTCAACAGC TAGGGAGCAG CTAGGCGCAA TGTGTGCGCT CTTTTAGCAA
4001  GGCTGCTAGG TCAGTGAACA ACAACTAGGG AGCAGCTTGG GGCGCTAAGT
4051  GCGCACTGAT GGGCAAAGCT GCTCAATCAG TGAACGTATG CTAGAGAATT
4101  TAAATACCCG CAGTTCGCAG GATTATGCAC CTCTCCGTGT GTCCTGCAAG
4151  TGTGGGCATG CGCAGCACTT TGCAGGGATA TGCTCTTCTG TGTGTGTTTT
4201  GCAAGTGTGG GCTTGCGCAC CCATGCTCCA CAGATATCCG TGTGTGGCGA
4251  AGAGGTTGGT GGACATGCTT TCATAGTTGC GACTTGTTTC ATGCTTTTGA
4301  AGGGGAGCAA GCCAAAGTTT TAGCAATGCT GCTGCATATG TCTCTGGATT
4351  GTGTAGAGGC TACCTTATTC TGCCATCCGC TTCCTCTAGA GCATGTGCTT
4401  ACCTCTTGTG TAAGGAGTTC TTGCTACTGA TTACCTCGGT GAGGCTTTGC
4451  TCGCGTGTGC TCGCATGCTC ACAGGTGCGG CTATTACGCA ATGTTGCCTG
```

FIGURE 6(ii)

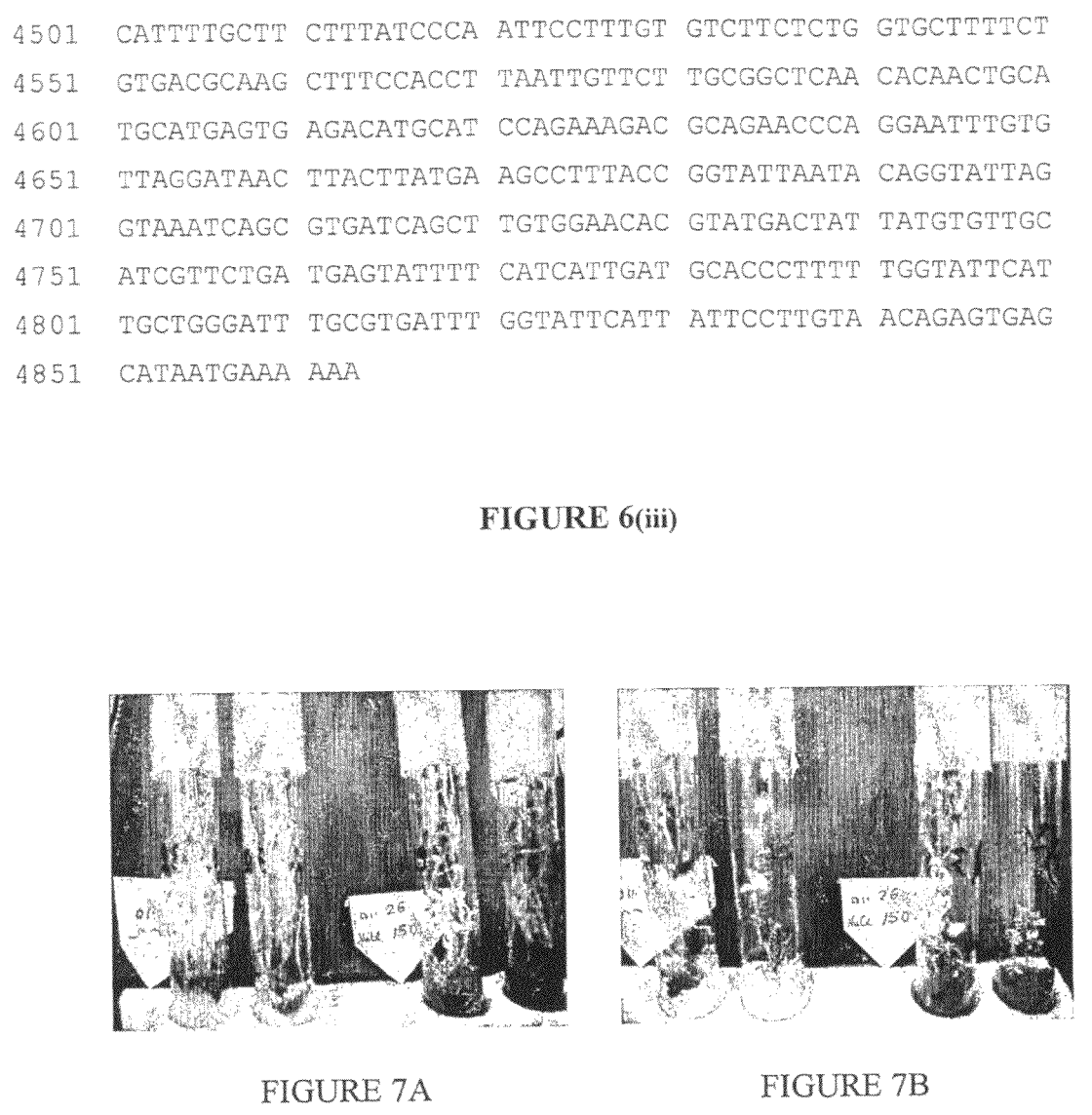

```
4501 CATTTTGCTT CTTTATCCCA ATTCCTTTGT GTCTTCTCTG GTGCTTTTCT
4551 GTGACGCAAG CTTTCCACCT TAATTGTTCT TGCGGCTCAA CACAACTGCA
4601 TGCATGAGTG AGACATGCAT CCAGAAAGAC GCAGAACCCA GGAATTTGTG
4651 TTAGGATAAC TTACTTATGA AGCCTTTACC GGTATTAATA CAGGTATTAG
4701 GTAAATCAGC GTGATCAGCT TGTGGAACAC GTATGACTAT TATGTGTTGC
4751 ATCGTTCTGA TGAGTATTTT CATCATTGAT GCACCCTTTT TGGTATTCAT
4801 TGCTGGGATT TGCGTGATTT GGTATTCATT ATTCCTTGTA ACAGAGTGAG
4851 CATAATGAAA AAA
```

FIGURE 6(iii)

```
1     atgtcgagtc tcgaagatat caagaacgag actgttgatc tggaaaaaat
51    tccgattgag gaagttttcc agcagctaaa atgttcaagg gaaggattga
101   caacgcagga aggggaggac aggattcaga tctttggccc caacaagctc
151   gaagagaaaa aggaaagcaa acttctgaag tttttggggt ttatgtggaa
201   tccactttca tgggtcatgg aaatggctgc aatcatggcc attgctttgg
251   ccaacggtga tggtaggcct ccggattggc aggattttgt tggtattatc
301   tgtctgttgg ttatcaactc taccatcagt tttatcgaag aaaacaatgc
351   tggtaatgct gctgctgctc ttatggctgg tcttgctcct aaaaccaagg
401   ttcttaggga tggaaagtgg agtgaacaag aagctgctat tcttgtccca
451   ggagatattg ttagcattaa attaggagac attatcccag ctgatgcccg
501   tctacttgaa ggtgatcctt taaaggttga ccaatctgct ctaactggag
551   agtcccttcc tgtaaccaag cacccgggtc aagaagtttt ctctggttca
601   acctgcaaac aaggagaaat cgaggcggtt gttattgcca ctggggttca
651   taccttcttc ggtaaagctg ctcaccttgt ggacagcact aaccaagttg
701   gacatttcca gaaggttctt acagccattg ggaacttctg tatctgttcc
751   attgctatcg gtatggtgat tgagatcatc gtcatgtatc cgatccaacg
801   ccgaaagtac agagatggaa ttgacaacct tttggtcctc ttgatcggtg
851   gtatccccat tgctatgcct acagtcttgt ccgtgaccat ggctattggg
901   tctcacaggt tgtctcagca aggtgccatc accaagcgta tgactgccat
951   tgaagagatg gcaggaatgg atgtcctgtg cagtgacaaa accgggacac
1001  taaccctcaa caaattgagt gtggacaaaa acttggtcga ggttttctgc
1051  aagggtgtgg agaaagatca agtcctatta tttgcagcta tggcttccag
1101  ggttgagaac caggatgcca ttgatgcagc catggttggg atgcttgctg
1151  atccaaagga ggctagagct ggaatcaggg aagttcactt ccttccattc
1201  aaccctgtgg ataagagaac tgctttgact tacattgacg gcagtggtaa
1251  ctggcacaga gtcagtaaag gtgctcctga gcagatcctc gaacttgcca
1301  aagccagcaa tgatcttagc aagaaggtgc tctccattat tgacaagtat
1351  gctgagcgtg gtcttaggtc gttggctgtt gctcgccagg tggtgccaga
1401  gaaaacaaag gaaagcccag gtgcgccatg ggaatttgtt ggcttgttgc
```

FIGURE 11(i)

```
1451  cactttttga tcccccaaga catgacagtg ctgaaacaat tcgacgggct
1501  ttgaatcttg gtgttaacgt caagatgatc actggtgacc aacttgctat
1551  tggtaaggaa actggtcgca gacttggaat gggaacaaac atgtatccat
1601  cttcggctct tcttggtaca cacaaagacg caaacctcgc atccattcct
1651  gttgaggagt tgattgaaaa ggctgatgga tttgccggag tcttcccaga
1701  gcacaaatac gaaattgtga aaaagttgca ggagaggaag catattgttg
1751  gaatgactgg tgatggtgtc aatgatgccc ctgctctaaa gaaagctgat
1801  atcggtattg ctgttgctga tgctacagat gctgctcgtg gtgcttcaga
1851  tatcgtgctc actgagcctg gactcagcgt tattatcagt gctgttctca
1901  ccagcagagc tattttccag agaatgaaga actatactat ctatgcagtc
1951  tcaatcacca tccgtattgt gtttggtttc atgcttattg ctttgatatg
2001  ggaatttgac ttctcagcct tcatggttct gatcattgcc attcttaacg
2051  acggtacCAT GATCGCCCTA TCCAAGGACC GTGTGGTGGC CTCTGTGTTG
2101  CCTAGCACCT GGAACCTCGC CACCATCTTC GTACCGGGTT TTGTCTACGC
2151  AATGTGGCTG ACTCTCTCCT CCTGGACACT GTACCAGGTG GCCACACATA
2201  GCACCTTCTT TGAACGCATG ACCCCACTGC CATCACTGAA CACCCAGCAT
2251  GCGACTCTCA TATCCTGGTG TGAGGATGAG ATCAGCAGCA AGTTGGGCGT
2301  CAATCCTCAA GATTCCCTGT GCACGTATCC AAGCTATGCT GATCAGCTGA
2351  ATGAATGCAA AGGCTCTGTG AGCCTGAGCT CACAGGTCCC TGGCGTGCCC
2401  ACCATTTTGG ATCAGTGCGT AACTGAGCAG CGCTACATTC GAGATGCCTT
2451  GACACGTGCC CTCATTTACA CCCACCTCTC TGTCTCTGGC CAAGCCGTTG
2501  TGTTTGTGGT GCGCACGTCC GGCTTCTCTC TGAAGGAAGT GGCAGGCGTC
2551  TCCACCTATG TCGCTTTCGC TCTTGCCCAG TTTGGTGCCA CAATGTTTGG
2601  CATCTTTGGC CTGGGAGGCT ATAACAAGCC CCGACAGAAT TTTGACAACT
2651  GCCAGTTCTG TGATTACTCC ACCCATAATC GCGTGCTGTT CTTTAACTCA
2701  GAGGTGGTGC CTCGCGCTGG TACAGAATCT GTCTACACTG CTTCTGTCAT
2751  TGGATGCGGA GGTTATGTCA TTGTCGCTTG GATCTGGGCT GCTCTGTTCT
2801  ACACTGCGCT GGATCCCTTG AAGTGGGGCT TGATGTGGAT CATGAACGAT
2851  GATGGCTTCA GGGACTAAAC TAGT
```

FIGURE 11(ii)

```
1    atgtcgagtc tcgaagatat caagaacgag actgttgatc tggaaaaaat
51   tccgattgag gaagttttcc agcagctaaa atgttcaagg gaaggattga
101  caacgcagga aggggaggac aggattcaga tctttggccc caacaagctc
151  gaagagaaaa aggaaagcaa acttctgaag tttttggggt ttatgtggaa
201  tccactttca tgggtcatgg aaatggctgc aatcatggcc attgctttgg
251  ccaacggtga tggtaggcct ccggattggc aggattttgt tggtattatc
301  tgtctgttgg ttatcaactc taccatcagt tttatcgaag aaaacaatgc
351  tggtaatgct gctgctgctc ttatggctgg tcttgctcct aaaaccaagg
401  ttcttaggga tggaaagtgg agtgaacaag aagctgctat tcttgtccca
451  ggagatattg ttagcattaa attaggagac attatcccag ctgatgcccg
501  tctacttgaa ggtgatcctt taaaggttga ccaatctgct ctaactggag
551  agtcccttcc tgtaaccaag cacccgggtc aagaagtttt ctctggttca
601  acctgcaaac aaggagaaat cgaggcggtt gttattgcca ctggggttca
651  taccttcttc ggtaaagctg ctcaccttgt ggacagcact aaccaagttg
701  gacatttcca gaaggttctt acagccattg ggaacttctg tatctgttcc
751  attgctatcg gtatggtgat tgagatcatc gtcatgtatc cgatccaacg
801  ccgaaagtac agagatggaa ttgacaacct tttggtcctc ttgatcggtg
851  gtatccccat tgctatgcct acagtcttgt ccgtgaccat ggctattggg
901  tctcacaggt tgtctcagca aggtgccatc accaagcgta tgactgccat
951  tgaagagatg gcaggaatgg atgtcctgtg cagtgacaaa accgggacac
1001 taaccctcaa caaattgagt gtggacaaaa acttggtcga ggttttctgc
1051 aagggtgtgg agaaagatca agtcctatta tttgcagcta tggcttccag
1101 ggttgagaac caggatgcca ttgatgcagc catggttggg atgcttgctg
1151 atccaaagga ggctagagct ggaatcaggg aagttcactt ccttccattc
1201 aaccctgtgg ataagagaac tgctttgact tacattgacg gcagtggtaa
1251 ctggcacaga gtcagtaaag gtgctcctga gcagatcctc gaacttgcca
1301 aagccagcaa tgatcttagc aagaaggtgc tctccattat tgacaagtat
1351 gctgagcgtg gtcttaggtc gttggctgtt gctcgccagg tggtgccaga
```

FIGURE 12(i)

```
1401 gaaaacaaag gaaagcccag gtgcgccatg ggaatttgtt ggcttgttgc
1451 cactttttga tcccccaaga catgacagtg ctgaaacaat tcgacgggct
1501 ttgaatcttg gtgttaacgt caagatgatc actggtgacc aacttgctat
1551 tggtaaggaa actggtcgca gacttggaat gggaacaaac atgtatccat
1601 cttcggctct tcttggtaca cacaaagacg caaacctcgc atccattcct
1651 gttgaggagt tgattgaaaa ggctgatgga tttgccggag tcttcccaga
1701 gcacaaatac gaaattgtga aaaagttgca ggagaggaag catattgttg
1751 gaatgactgg tgatggtgtc aatgatgccc ctgctctaaa gaaagctgat
1801 atcggtattg ctgttgctga tgctacagat gctgctcgtg gtgcttcaga
1851 tatcgtgctc actgagcctg gactcagcgt tattatcagt gctgttctca
1901 ccagcagagc tattttccag agaatgaaga actatactat ctatgcagtc
1951 tcaatcacca tccgtattgt gtttggtttc atgcttattg ctttgatatg
2001 ggaatttgac ttctcagcct tcatggttct gatcattgcc attcttaacg
2051 acggtaccat catgacaatc tcaaaggaca gagttaagcc atctcccaca
2101 cctgatagct ggaaacttaa agaaattttt gctactggag tcgttctagg
2151 aggctaccag gccatcatga ctgttatttt cttctgggcg gcgcacCATA
2201 GCACCTTCTT TGAACGCATG ACCCCACTGC CATCACTGAA CACCCAGCAT
2251 GCGACTCTCA TATCCTGGTG TGAGGATGAG ATCAGCAGCA AGTTGGGCGT
2301 CAATCCTCAA GATTCCCTGT GCACGTATCC AAGCTATGCT GATCAGCTGA
2351 ATGAATGCAA AGGCTCTGTG AGCCTGAGCT CACAGGTCCC TGGCGTGCCC
2401 ACCATTTTGG ATCAGTGCGT AACTGAGCAG CGCcacgagc taatgggtgc
2451 ggtgtactta caagttagta tcattagtca agctctgatc ttcgtcacaa
2501 gatcaaggag ttggtctttt gttgaacgtc ctggagcatt gctgatgatt
2551 gctttcctca ttgcacaact gattgctact ttgattgcgg tttacgccaa
2601 ctgggaattt gcaaagatta ggggtattgg atggggatgg gctggtgtga
2651 tctggctata cagtattgtc acatacttcc cattggacgt tttcaagttt
2701 gccattcgat acatcttgag cggaaaggcg tggctcaact tgtttgagaa
2751 caagacggct ttcacgatga agaaagatta cggaaaagaa gagagagagg
```

FIGURE 12(ii)

```
2801  ctcaatgggc acttgctcaa aggacacttc acggtttaca gccaaaagaa
2851  gctgttaaca tcttccctga gaaaggaagt tacagagaat tgtctgagat
2901  cgctgagcaa gctaagagaa gagctgagat cgctaggctt agggagctgc
2951  acacactcaa gggacatgtg gaatcagtcg tgaagctaaa gggcttggac
3001  attgaaactc ccagtcacta cactgtgtag
```

FIGURE 12 (iii)

```
1     AGCCCGAAGG CGGCTGTTTG AGCTAGGAGT CACTAGGATT ATTGGCCGGG
51    CGAACACAGG AAAGACAGGC AGCAGCAGCA TCTGCGGACA CTCACTGCCT
101   TTTTGCAGCC CAGACCTGCA CGAACGACAA GGGAGACAGC CCCGCCAGAG
151   CAGCAGGCTC AAATGGGCCT GACCATTGAG CCCCCCCATG ATCACGGACT
201   GACAACCCAG GAGGTTGAGC AGCTGCAGAA GGAGTGGGGT CTCAACCATG
251   TCGCTGCCAA GACGATCCCG GAGTGGAAGA AAATCCTTGA TCGCTACCTG
301   GACTGGGTGT CGCTCATCAT TCTCATTTCC GCCATCATTT CCGCGGCGGT
351   GCCCGTCAAT GGCGACCAGG GCTGGACCTC CTTTGTGATG CTCATCCTCG
401   AGCTGCAGTT CGTGGTGTGG ATGGGCTACT ACTCGGACCG GAATGCGGGA
451   GATGCCGTCG CTGAGCTTGC GGCCCTGTCT GCACCCATGT GCCACTGCTT
501   GCGGAACGGG AAGTGGGGCA GCCTGCCGGT GAAGGAGCTG GTGCCTGGCG
551   ACATCATTGG CCTCAAGGGT GGTGATGTCA TCCCAGCAGA CAGTAAGCTC
601   ATTGGAGAGG GAGAGCCCCT GAAGATTGAT GAGTCCTCAC TGACAGGGGA
651   GTGCCTTGCA GTCACGAGGC ACCCTGGCCA AGAGATTCTT GCGGGTGCTG
701   TGGTGGTGTC TGGTGAGCTG GACGCCATGG TCACTGCTAC TGGTGTGAAC
751   TCCTTCTTTG GTAAGACAAT GGCCTTGCTG GCCGTCCCCC CCGAGCGTGG
801   ACACTTGCAG CAGGTGCTCA ACCGTGTGTC CATTGCCCTG GCCCTGTTTG
851   CCGTCGCTGG CTGCGCCATC ATTCTGGGTG TGCTCACCGG TCACTACGAC
901   AACCCCCCTG GGTATTCCAT CGTCACTGTC TTCGTCATTT TCACCTCCGT
951   GGTGCCCATT GGCATGCCTG TGGTCACCAC CACTGTGCTG GCTGTGGGTG
1001  CCCGGGAGAT GGCCCGCGAG AAGGCCATTG TCACAAGGCT GTCAGCCCTG
1051  GAAGAGATGT CTGGTATGGA GGTGCTGGCT TCCGATAAGA CTGGCACTCT
1101  CACCCTTAAC CAGCTGAGCC TTGACAAGGA GGACATCCTG AACTGGGGTA
1151  CCCATACCAA GGATGATGTG CTGCTTTACT CCTGCCTGAG TGCCAAATGG
1201  GAGAACAATG ATGCCATCGA TAAAGCCGTG ACCAACTCCC TGGGAGACAA
1251  GAAGTATGTT GCCGGCTACA AGATCACCAA GTTCAGCCCC TTCAACCCCG
1301  TGGACAAGAA GACCACCGCC CACACCATCA CCCCCACTGG CGAGAAGCTG
1351  ATCACCACCA AGGGTGCCCC CCAGATCATT GGTGACATGC TGGCTGACCC
```

FIGURE 14(i)

```
1401 TGCTGCACGC CAGGCCTGCG CAGACTACAT TGCAGAGCGC GCCTCCCGCG
1451 GCCTGCGCTC CCTGGGTGTT GCCCGCTCCG ATGATGATGG CCAGACCTGG
1501 TCCCTGGTGG GCCTCATCTC CTTGCTGGAC CCCCCTCGCC CTGACTCTGG
1551 AGAGACCATC AAGCTGGCCC AGTCCATGGG TGTGGCAGTG AAGATGGTGA
1601 CAGGCGACCA GTTTGCCATT GCCGTGGAGA CCTGCAAGCG CCTGGGCATG
1651 GGCTCTACCA TCATGGAGGG CAAGACGGTC ATGGCAGGCC TGAAGGGCGG
1701 CGATGAGGGC AAGCCTGACC CTGTCCTGAT CCAGCACTGC GACGAGAGTG
1751 ATGGCTTTGC CGGCGTGTAC CCGGAGCACA AGCACATGAT TGTGTCAGCA
1801 TTGCAGGCCA AGGGGCGCCT GGTTGGTATG ACAGGTGATG GTGTGAACGA
1851 TGCTCCCGCC CTGAAGAAGG CCAACGTCGG TATTGCCGTC GCTGGTGCCA
1901 CATCTGCTGC CAAGGGTGCT GCAGATATCA TCCTGACCAG GGAGGGTATC
1951 AGCACCATCA TCATTGCCAT CGTGCGCTCC CGCAAGATCT TCCGCCGCCT
2001 GGAGATGTAC ATCATCTACC GCATGGCCTC CTCCGTGCTC ATCCTGGGCT
2051 TCTTCTTCTT TGCCATCCTC ATCTTTGACT TCGAGATCCC CACCTGGATC
2101 CTGGTGCTGA TTTCCATGCT CAACGACGCC TCCGTCATTG CCACCTCCTA
2151 CGACGCGGTG CACAGCTCTG ACTACCCCCT GCACTGGAAC ATGACCAAGG
2201 ATCTGGCGAT TGCCTTCTCC ATTGCCATGG TGGGCATTGT GGGCAACGTG
2251 CTGCTGGTGC CCTTCGTCCG CCCTGATCTG TGGTTTGAGT GGCCTGAGCT
2301 TGACACCGAG CCTGCGCTCA AGACCCCCCC TGACAATGGC GTGTCCACCT
2351 CTGGCAAGGA GTCGGCCCTG ATCTTCCTGT CCCTCTCCGG CATGGTCCAG
2401 CTGAACATCA TCCTGACCCG CAACCCCTCC TTCTGGTGGC ACTTCAGCAA
2451 GAAGAGCGCC CCCAAGCCGT CCCCCATCTT GCTGGTCCCT GTGACATGCT
2501 TCCTGGGTGG TTCCACCTTC ATGTCCGTGT ACTGGAACGG CAACATCAAG
2551 CCTGACGGAC AGCGCTACCT GTTTGAGGGC GCAGGCTGGC ACGCGGTGCT
2601 GCTGGTGTGG CCCTATGTTT TCGTCTTCTG GGTCATCGCT GACTTCTTCA
2651 AGGTGGCCAT CAGCTCCGTC TTCGTGAAGG CCGACCTGAT CAAGGATGAG
2701 CTCAAGGGCC ACATTGATGG TAAGGAGAAG ACCCCCGGCT GGGTCAAGGC
2751 CCTGGACTGG CCTGGTGAGA CCGCCGACAA GATCAGTGAC AAGATTGAGG
2801 CCTGCTTCGA CGGCATGTGC TCTTGCTTTG AGAAGAAAGA GAAGAAGGCC
```

FIGURE 14(ii)

```
2851  AAGTTCCAGC GCACGTCCGT CGTGTCTGAG AAGGAGGGAG AGGGCCAGGT
2901  GCATGTGCAA GTGGAGGGTG AGAAGCAGGC CTAATCAAGC CCTACGGGTC
2951  ATGGGCCTGC TCATGCAGTG AGCGCATGCT CAGCTGCAGG TACGTCACGC
3001  AGCATGAGCC ACAATCCGAA TGTCTGCTCG TGTGGTTTGG AAGGGGAAGG
3051  CAGGCGCACG ATGGAGGGGG GTTGCCAGCT TACATTTTTG TCTCGAGTGC
3101  GCCTCTTTTG CTTGGTTGTA GAGTGACTTG GTGGTTGAGG CAGACGGAGG
3151  GCCTCCCATC GATCAATCCC ACACGATTCT CTTTTACTGT GCGTTAAAGT
3201  TTTGCCAAAC TAGGCCGTAC ACACCTGCCC GCTCACGCCA TTTTGTTTGG
3251  CTTCCTGGCA ATGAGTTGTA GCCTGTGAGC GCATTTAAAA GTACTGCATA
3301  TGCACTGTTG TGCTATAGGA TCTAAAACAA CAATGGAGGC GTGCGTGTCT
3351  GTAGTTTGTC GTGGAGGCAC GTGCTCATGC ATGCAATTGT CCTGGTGCCT
3401  CAGGCCTCCT CCCCTCCTTG TATGAAAGAT TGCTTTTTAG CTTAGCGTCT
3451  GATTTATGGC GGTGGAGGAG GAGACAACAT AGCAGCAGAA GTTTCTACGG
3501  TGTTGTGGCG TGTGCTCATC CGTTAGCATT CTACAGTTGC CACGCTAGGT
3551  TGCTGCCTCC GGGCATGTTC CAGTTGGTCC TCTCAGATTG CATGATGCAA
3601  TTTCCGTCTG AAAGCATGCG TGAGGGCACA TTTCTGCCCC TGGCATACAT
3651  ACATGTAGCT GTCTTCCACA GTGGATGGGT AGGTAGTTCC GGAATGGGCG
3701  GGCACGCGCC ATGACCAGCT GGGTCCACTA GGGTCAGGAG ATGCCCAGTC
3751  CCGATATCCT TCCATTTTGC GACGCATGAA ACACATCCTG AGTGTCGGCT
3801  TAGCAGGAGT GTGTTCCAGG AGCAAGCTCC AGCTTGCTTT ATGAGGCAGG
3851  GGAATGGGTG TCAATGCCCA GCGCGTGCCC TTCCTGAAGG CAGGGGCTGG
3901  CCGGCATGCC TATAGTATGT ACTTTAATTT CCGTATGATT TGTTCAGCAG
3951  GCTGTGTGTT TGCTCGATAA ACTCTCATTT TATTGCGGTC ATTTGGACCT
4001  GTTTCTACAC TCAAAACCTA ACTTTCAACT CTATAGGGTG TTGGTTTTTA
4051  CACTTCGGTT GTGCACGAGA AAGGTAGCCT GGTTTTCAGT GGGGCGCTGT
4101  AAGTGTACAC AGTTTCAAAA AAAAAAAAAA AAAAAAAA
```

FIGURE 14(iii)

SALT RESISTANT TRANSGENIC PLANTS

RELATED APPLICATION DATA

This application is the U.S. national stage of PCT/IL2005/000932 filed on Sep. 1, 2005, which is based on and claims the benefit of U.S. Provisional Patent Application No. 60/606,415 filed on Sep. 2, 2004, which is incorporated herein in its entirety by this reference.

FIELD OF THE INVENTION

The present invention relates to transgenic plants capable of growing in conditions of high salinity. More specifically, the present invention relates to transgenic plants having high salt tolerance conferred by the expression of a plasma membrane (PM)-ATPase from the highly salt resistant green alga *Dunaliella.*

BACKGROUND OF THE INVENTION

The progressive salinization of agricultural soils poses a major limitation for the growth and productivity of agricultural crops. Although engineering technology involving drainage and supply of high quality water has been developed to overcome this problem, the existing methods are extremely costly and time-consuming. In many instances, due to the increased need for extensive agriculture, neither improved irrigation efficiency nor the installation of drainage systems is applicable. Moreover, in the arid and semi-arid regions of the world water evaporation exceeds precipitation. These soils are inherently high in salt and require vast amounts of irrigation to become productive. Since irrigation water contains dissolved salts and minerals, application of water further compounds the salinity problem.

Current attempts to enhance the salinity tolerance of model and crop plants are based on conventional breeding and selection of resistant variants. However, such breeding techniques typically require years to develop, are labor intensive and expensive. Moreover, thus far, these breeding and selecting strategies did not result in the mass production of tolerant varieties, suggesting that conventional breeding practices are not sufficient.

An alternative and attractive approach involves the genetic engineering of transgenic crops having enhanced salt tolerance. In recent years, advances in molecular biology have allowed mankind to manipulate the genetic complement of animals and plants. Genetic engineering of plants entails the isolation and manipulation of genetic material (typically in the form of DNA or RNA) and the subsequent introduction of the genetic material into plants. Such technology has led to the development of plants with increased pest resistance, plants that are capable of expressing pharmaceuticals and other chemicals and plants that express beneficial agricultural traits. Advantageously, such plants not only contain genes of interest, but remain fertile.

Sodium ions in saline soils are toxic to plants due to their adverse effect on potassium nutrition, cytosolic enzyme activities, photosynthesis and metabolism. Different mechanisms function cooperatively to prevent accumulation of sodium ions ($Na^+$) in the cytoplasm of plant cells, namely restriction of $Na^+$ influx, active $Na^+$ efflux and compartmentalization of $Na^+$ in the vacuole. There is a wide spectrum of plant responses to salinity that are defined by a range of adaptations at the cellular and the whole plant levels, however, the mechanism of sodium transport appears to be fundamentally similar in many plant species. At the cellular level, sodium ions are extruded by plasma membrane $Na^+/H^+$ antiporters that are energized by the proton gradient generated by the plasma membrane $H^+$-ATPases (PM $H^+$-ATPases). Cytoplasmic $Na^+$ may also be compartmentalized by vacuolar $Na^+/H^+$ antiporters. These transporters are energized by the proton gradient generated by the vacuolar $H^+$-ATPase and $H^+$-PPiase.

The response of plants to salt stress has previously been studied in model plant species with sequenced genomes, including *Arabidopsis thaliana* and in rice (Goff S A, et al. (2002) Science 296:92-100; Yu J, et al. (2002) Science 296: 79-92). Differential genomic screens carried out in *Arabidopsis* and rice have shown that plants respond to salt stress by up-regulation of a large number of genes involved in diverse physiological functions.

PM $H^+$-ATPases are the primary ion pumps in plasma membranes of plants and fungi. They are encoded by a large multigene family, amounting to 12 members in the salt-sensitive plant *Arabidopsis thaliana* alone. PM $H^+$-ATPase isoforms are expressed in different tissues and control diverse physiological functions (Palmgren M G (2001) *Ann Rev Plant Physiol Plant Mol Biol* 52:817-45; Sekler I & Pick U (1993) *Plant Physiol* 101:1055-1061). In yeast such as *Saccharomices pombe*, PM $H^+$-ATPases energize $Na^+$ extrusion via a $Na^+/H^+$ antiporter by generating the protomotive force across the plasma membrane. A large body of evidence suggests that PM $H^+$-ATPases also contribute to salinity tolerance. In plants, salt stress induces activation and enhanced expression of PM $H^+$-ATPases, either by over-expression of specific enzyme isoforms, or by activation of existing enzymes (Reuveni M, Bressan R A & Hasegawa P M 1993 *J Plant Physiol* 142:312-318); Zhang J S et al., (1999) *Theor Apll Genet.* 99:1006-1011; Kerkeb L, Donaire J P & Rodriguez-Rosales M P (2001) *Physiologia Plantarum* 111:483-490). Two specific isoforms of PM $H^+$-ATPases encoding genes were identified in tomato and in *A. thaliana* which are specifically involved in the response to salt stress (Kalampanayil B D and Wimmers L E (2001) *Plant, Cell, Environment* 24:999-1005; Vitart V et al., (2001) *The Plant J* 27:191-2001).

A comparison of ion distribution in cells and tissues of various plant species indicates that a primary characteristic of salt-tolerant plants is their ability to exclude sodium out of the cell and to take up sodium and sequester it in the cell vacuoles (Niu, X., et al., 1995 *Plant Physiol.* 109:735-742). This strongly suggests that $Na^+/H^+$ antiporter from salt-tolerant plants have functionally more effective sodium transport systems compared with salt-sensitive plants such as *Arabidopsis.*

Several sodium transport systems associated with salt tolerance have been characterized in different organisms and a few of the genes involved in this process have been identified and used to generate plants having enhanced salt-resistance. For example, a homologue of sodium antiporter (AtNhx1) from the salt-sensitive plant *Arabidopsis thaliana* has been identified and characterized. Over expression of AtNhx1 in *Arabidopsis* (Apse, M P et al., (1999) *Science* 285:1256-1258) as well as in fission yeast shows increased salt tolerance due to better performance of salt compartmentation into the vacuole. Zhang et al have shown that over expression of vacuolar $Na^+/H^+$ antiporter in *A. thaliana* and tomato plants led to a significant enhancement in salinity tolerance (Zhang H X & Blumwald E (2001) *Nature Biotechnology* 19:765-768). Shi et al demonstrated that over expression of $Na^+/H^+$ antiporter SOS1 in plant plasma membranes improves salinity tolerance in *A. thaliana*, suggesting that a plasma membrane-type $Na^+/H^+$ antiporter is essential for plant salt tolerance. (Shi H, Lee B H & Zhu J K (2003) *Nat Biotechnology* 21:81-85).

International Patent Application No. WO 91/06651 discloses a single gene (sod2) encoding for a $Na^+/H^+$ antiporter that has been shown to confer sodium tolerance in fission yeast, although the role of this plasma membrane-bound protein appears to be only limited to yeast.

US Patent Application No. 20040040054 discloses polynucleotides encoding plant $Na^+/H^+$ antiporter polypeptides isolated from *Physcomitrella patens* and methods of applying these plant polypeptides to the identification, prevention, and/or conferment of resistance to various plant diseases and/or disorders, particularly environmental stress tolerance in plants, specifically salt stress.

US Patent Application No. 2002178464 discloses transgenic plants transformed with exogenous nucleic acid which alters expression of vacuolar pyrophosphatases in the plant, wherein the transgenic plants are tolerant to a salt. Specifically, the exogenous nucleotide encodes a vacuolar pyrophosphatase $H^+$ pump, AVP1.

International Patent Application No. WO 03/031631 discloses nucleic acids and nucleic acid fragments encoding amino acid sequences for salt stress-inducible proteins, protein phosphatases mediating salt adaptation in plants, plasma membrane sodium/proton antiporters, salt-associated proteins, glutathione peroxidase homologs associated with response to saline stress in plants, and early salt-responding enzymes such as glucose 6-phosphate 1 dehydrogenase and fructose-biphosphate aldolase in plants and the use thereof for, inter alia, modification of plant tolerance to environmental stresses and osmotic stresses such as salt stress modification of plant capacity to survive salt shocks, modification of compartmentalization of sodium in plants, for example into the plant cell vacuole, modification of sodium ion influx and/or efflux, modification of plant recovery after exposure to salt stress, and modification of plant metabolism under salt stress.

These studies demonstrate that, using combination of breeding strategies and genetic manipulation, it is be possible to generate plant crop having enhanced salt tolerance. However, all of the aforementioned methods rely on the isolation, characterization and over expression of genes from plant sources, and accordingly the success of such approaches relies on the intrinsic adaptation of the plant genetic material, and the encoded proteins, to salt environment. Since plants are not well adapted to highly saline conditions, the success of these approaches has been limited.

Exceptionally salt tolerant (halotolerant) organisms may provide useful for identification of basic mechanisms that enhance salinity tolerance. A special example of adaptation to variable saline conditions is the unicellular green algae *Dunaliella*, a dominant organism in many saline environments, which can adapt to practically the entire range of salinities. *Dunaliella* responds to salt stress by massive accumulation of glycerol (its internal osmotic element), enhanced elimination of $Na^+$ ions, and accumulation of distinct proteins (Pick U et al. In A Lauchli, U Luthge, Eds. Salinity: Environment-Plants Molecules, Ed Acad. Pub. Dordrecht. Kluwer, pp 97-112, 2002). Since the cells of this genus do not possess a rigid cell wall, they respond to changes in salt concentration by rapid alterations in cell volume and then return to their original volume as a result of adjustments in the amounts of intracellular ions and glycerol. It has been reported that the adaptation to extreme salinity involves short-term and long-term responses. The former include osmotic adjustment by accumulation of large amounts of intracellular glycerol and efficient elimination of $Na^+$ ions by plasma membrane transporters. The latter involves synthesis of two extrinsic plasma membrane proteins, a carbonic anhydrase and a transferrin-like protein. These proteins are associated with acquisition of $CO_2$ and Fe, respectively, whose availability is diminished by high salinity. In addition, Ajalov et al reported on the isolation of a 64 kDa and 28 kDa salt-induced polypeptides from *Dunaliella salina* (Ajalov et al. (1996), *Biochemical Society Transactions,* 24(4), 5345).

Due to its remarkable ability to adapt to highly saline conditions, *Dunaliella* serves as a valuable model for the identification of basic mechanisms in salinity tolerance.

The success of current plant breeding strategies which are based on genetic manipulation of genes from plant sources has been limited due to the limited capability of plants to adapt to saline conditions. There remains a need in the art to develop genetic engineering approaches that are superior to current techniques, and that would yield transgenic plants having high salt tolerance that are capable of growing in conditions of high salinity.

SUMMARY OF THE INVENTION

The present invention provides a transgenic plant comprising one or more plant cells transformed with an exogenous nucleic acid encoding a *Dunaliella* plasma membrane (PM)-ATPase or a fragment, homolog or variant thereof. The PM-ATPase is preferably a *Dunaliella* $H^+$-ATPase, a *Dunaliella* $X^+$-ATPase, or the PM-ATPase can also be a chimera of a plant PM-ATPase and a *Dunaliella* PM-ATPase. The transgenic plant has increased tolerance to salt as compared to a corresponding non-transgenic plant. The invention is based in part on the surprising discovery that transformation of tobacco plants with a nucleic acid encoding a PM-ATPase (e.g. $H^+$-ATPase) isolated from the highly salt tolerant green water alga *Dunaliella* (e.g. *Dunaliella acidophila* and *Dunaliella salina*), gives rise to a transgenic plant having an increased tolerance to salt as compared to a corresponding non-transgenic plant. The salt tolerance correlates with the expression of the *Dunaliella* PM-ATPase in the transgenic plants.

Applicants have characterized and cloned several PM-ATPase genes from the extremely acidophilic/halophilic algae *Dunaliella acidophila* and *Dunaliella salina*, which differ from plant PM-ATPases in distinct kinetic and structural features. The nucleic acids were either isolated from *Dunaliella* or constructed as chimeras of plant and *Dunaliella* ATPase, and were used to confer salt resistance in plants.

The following genes were isolated from *Dunaliella* in accordance with a preferred embodiment of the present invention: A) a PM $H^+$-ATPase (SEQ ID NO:1 (FIG. 2); SEQ ID NO:2 (FIG. 3) and SEQ ID NO:3 (FIG. 6)); and B) a PM $X^+$-ATPase (SEQ ID NO:6, FIG. 14).

The following chimeric $H^+$-ATPase genes comprising a first portion derived from a plant source and a second portion derived from *Dunaliella* were constructed in accordance with a preferred embodiment of the present invention: A) an H-ATPase chimera of the plant *Arabidopsis thaliana* $H^+$-ATPase (bases 1-2057) and a *Dunaliella acidophila* C-terminal $H^+$-ATPase (bases 2058-2847) was constructed (SEQ ID NO: 4, FIG. 11); and B) an $H^+$-ATPase chimera of the plant *Arabidopsis thaliana* $H^+$-ATPase (bases 1-2195 and 2434-3030) and a *Dunaliella acidophila* trans-membrane loop 7-8 (bases 2196-2433), was constructed (SEQ ID NO: 5, FIG. 12).

The optimal growth conditions for most *Dunaliella* species range from 0.5 to 2M NaCl, well above the maximal salinity range for growth of most plant species, which show reduced growth rates and other salt stress symptoms at a salinity of about 0.1M. Therefore, *Dunaliella* PM-ATPases are adapted to function at high salinity. The special features of these enzymes are utilized in order to confer salt-tolerance in plants. For example, expression of *D. acidophila* PM $H^+$-ATPase under the 35S promoter in tobacco greatly enhances their salinity tolerance in correlation with expression of the $H^+$-ATPase protein.

The transgenic plants of the present invention are by far superior as compared with other salt-tolerant plants known in the art. Specifically, all previous attempts rely on the over-expression of genes from plant sources, and accordingly the success of such approaches relies on the intrinsic adaptation of the plant genetic material to salt environment. The present invention takes advantage of the special features of the *Dunaliella* PM-ATPases which have adapted to function at very high salt concentrations, in order to confer salt-resistance in plants.

Thus, in one embodiment, the present invention relates to a transgenic plant transformed with exogenous nucleic acid encoding a *Dunaliella* PM-ATPase or a fragment, homolog or variant thereof. The transgenic plant has an increased tolerance to salt as compared to a corresponding non-transgenic plant. Preferably, the PM-ATPase is a PM-$H^+$-ATPase or a PM-$X^+$-ATPase, or a fragment, homolog or variant thereof.

The PM-ATPase is preferably a *Dunaliella salina* PM-ATPase or a *Dunaliella acidophila* PM-ATPase, although it is contemplated that any *Dunaliella* salt-resistant species can be used as a source for the PM-ATPase.

In one preferred embodiment, the PM-ATPase is a *Dunaliella acidophila* $H^+$-PM-ATPase, and the nucleic acid comprises a polynucleotide having a sequence as set forth in SEQ ID NO:1 [GenBank and EMBL Accession No. U54690, starting nucleotide No. 175, end nucleotide No. 3638]. In another preferred embodiment, the PM-ATPase is a *Dunaliella acidophila* $H^+$-PM-ATPase, and the nucleic acid comprises a polynucleotide having a sequence as set forth in SEQ ID NO: 2 [GenBank and EMBL Accession No. U54690, starting nucleotide No 175, end nucleotide No 3126]. In another preferred embodiment, the PM-ATPase is a *Dunaliella salina* $H^+$-PM-ATPase, and the nucleic acid comprises a polynucleotide having a sequence as set forth in SEQ ID NO:3. In yet another preferred embodiment, the PM-ATPase is a *Dunaliella salina* $X^+$-PM-ATPase, and the nucleic acid comprises a polynucleotide having a sequence as set forth in SEQ ID NO: 6.

In yet another preferred embodiment, the PM-ATPase is a chimera of an *Arabidopsis thaliana* $H^+$-ATPase [GenBank and EMBL Accession No. J05570A] and a *Dunaliella acidophila* $H^+$-ATPase, and the nucleic acid comprises a chimera of an *Arabidopsis thaliana* $H^+$-ATPase (bases 1-2057) and a *Dunaliella acidophila* C-terminal area (bases 2058-2847) as set forth in SEQ ID NO: 4.

In yet another preferred embodiment, the PM-ATPase is a chimera of an *Arabidopsis thaliana* $H^+$-ATPase and a *Dunaliella acidophila* $H^+$-ATPase, and the nucleic acid comprises a chimera of an *Arabidopsis thaliana* $H^+$-ATPase (bases 1-2195 and 2434-3030) and a *Dunaliella acidophila* trans-membrane loop 7-8 (bases 2196-2433) as set forth in SEQ ID NO: 5.

In another aspect the present invention relates to a nucleic acid encoding a PM-ATPase, comprising a first portion encoding a plant PM-ATPase or a fragment thereof, and a second portion encoding a *Dunaliella* PM-ATPase or a fragment thereof. In one embodiment, the PM-ATPase is a chimera of an *Arabidopsis thaliana* $H^+$-ATPase and a *Dunaliella acidophila* $H^+$-ATPase, and the nucleic acid comprises a chimera of an *Arabidopsis thaliana* $H^+$-ATPase (bases 1-2057) and a *Dunaliella acidophila* C-terminal area (bases 2058-2847) (SEQ ID NO:4). In another embodiment, the PM-ATPase is a chimera of an *Arabidopsis thaliana* $H^+$-ATPase and a *Dunaliella acidophila* $H^+$-ATPase, and the nucleic acid comprises a chimera of an *Arabidopsis thaliana* $H^+$-ATPase (bases 1-2195 and 2434-3030) and a *Dunaliella acidophila* trans-membrane loop 7-8 (bases 2196-2433) (SEQ ID NO:5). The present invention also provides constructs, vectors and plant transformation vectors comprising the chimeric nucleic acids.

The present invention also relates to a method of producing a transgenic plant having an increased tolerance to salt as compared to a corresponding non-transgenic plant. The method comprises (a) transforming a plant cell with exogenous nucleic acid encoding a *Dunaliella* PM-ATPase; and (b) regenerating the transformed cell into a plant having an increased tolerance to salt as compared to a corresponding non-transgenic plant.

The present invention also relates to a method of modifying plant capacity to survive salt shock, comprising the step of introducing into one or more cells of a non-transgenic plant an exogenous nucleic acid encoding a *Dunaliella* PM-ATPase, thereby producing a transgenic plant having modified (e.g. enhanced) capacity to survive salt shock.

Still another aspect of the invention relates to a method of modifying plant recovery after exposure to salt stress, comprising the step of introducing into one or more cells of a non-transgenic plant an exogenous nucleic acid encoding a *Dunaliella* PM-ATPase, thereby producing a transgenic plant having a modified plant recovery potential after exposure to salt stress.

The present invention also relates to a plant cell transformed with exogenous nucleic acid encoding a *Dunaliella* PM-ATPase. Furthermore, also encompassed by the present invention is a plant seed transformed with exogenous nucleic acid encoding a *Dunaliella* PM-ATPase. The plant seed is advantageously used for breeding a transgenic plant having an increased tolerance to salt as compared to a corresponding non-transgenic plant.

The PM-ATPase nucleic acid can be incorporated into a plant transformation vector which is incorporated into one or more plant cells and used to transform wild type plants.

Preferably, the transformed transgenic plant of the present invention expresses the polypeptide product of the PM-ATPase nucleic acid. The expression may be monitored by conventional methods known to a person skilled in the art, for example by extracting proteins from the plasma membrane of the transgenic plants and testing with antibodies directed against the *Dunaliella* PM-ATPase Any suitable plant can be used to produce the transgenic plants of the present invention. Non-limiting examples include tobacco, maize, wheat, rye, oat, triticale, rice, barley, soybean, peanut, corn, cotton, rapeseed, canola, manihot, pepper, sunflower, tagetes, Solanaceous plants, potato, eggplant, tomato, *Vicia* species, pea, alfalfa, sorghum, cucumber, lettuce, turf grass, ornamental, coffee, cacao, tea, *Salix* species, oil palm coconut, perennial grass and a forage crop. A currently preferred plant is a tobacco plant or a potato plant.

As mentioned above, the transgenic plants are highly salt-resistant, and are able to grow in a concentration of a salt that inhibits growth of a corresponding non-transgenic plant, for example a concentration of salt in the range of from about 0.1M to about 0.55M, typically at a salt concentration ranging from about 0.2M to about 0.3M.

For example, the transgenic plants of the present invention are adapted to growth in salt water, an environment typically too saline for many plant species. For example, in one embodiment, the transgenic plants of the present invention are adapted to grow in seawater.

The present invention thus provides novel transgenic plants which are capable of surviving and thriving in a highly saline environment. By taking advantage of the special features of a *Dunaliella* PM-ATPase, an enzyme adapted to survive and function in highly saline conditions, highly salt-resistant transgenic plants are obtained, which are superior to any salt-tolerant plants utilized hitherto.

BRIEF DESCRIPTION OF THE DRAWINGS

The invention will be understood from the following detailed description in conjunction with the following appended drawings:

FIG. 2 shows the sequence of *D. acidophila* PM $H^+$-ATPase gene (SEQ. ID NO:1).

FIG. 3 shows the sequence of truncated *D. acidophila* PM $H^+$-ATPase gene (SEQ. ID NO:2).

FIG. 4 is a picture of transformed and control tobacco plants grown with or without salt. FIG. 4A: Control without salt (left) and transformed plants grown in the presence of 250 mM NaCl (right). FIG. 4B: Control (left) and transformed plants (right) grown in the presence of with 250 mM NaCl.

FIG. 5 is a Western blot showing expression of *D. acidophila* $H^+$-ATPase genes (Da or DaT) in tobacco plants grown in the presence of 250 mM NaCl. C—proteins isolated from control plant; C(+)—proteins isolated from control plant grown in the presence of NaCl; Da—proteins isolated from transgenic plant with Da gene grown in the presence of NaCl; DaT—proteins isolated from transgenic plant transformed with Da Truncated gene grown in the presence of NaCl.

FIG. 6 shows the sequence of *D. salina* PM H-ATPase gene (SEQ. ID NO:3).

FIG. 7 shows the effect of salt (150 mM) on growth and appearance of in vitro potato plants: FIG. 7A-*transgenic* and FIG. 7B-*control* (non-transgenic). Plants were treated with salt for 26 days. The tube pair on the left in each panel was not treated with salt.

FIG. 11 shows the sequence of chimeric gene of the 5' area (first 2057 bases) of $H^+$-ATPase gene from *Arabidopsis thaliana* with the *Dunaliella acidophila* C-terminal area (bases 2058-2847) (SEQ ID NO: 4). *Arabidopsis thaliana* sequence is shown in lower case. *Dunaliella acidophila* sequence is shown in upper case.

FIG. 12 shows the sequence of chimeric gene of the *Arabidopsis thaliana* $H^+$-ATPase (aha-2) (bases 1-2195 and 2434-3030) including *Dunaliella acidophila* trans-membrane loop 7-8 ((bases 2196-2433) (SEQ ID NO: 5). *Arabidopsis thaliana* sequence is shown in lower case. *Dunaliella acidophila* sequence is shown in upper case.

FIG. 14 shows the sequence of *D. salina* PM $X^+$-ATPase gene (SEQ ID NO:6).

DETAILED DESCRIPTION OF THE INVENTION

Figure 1:
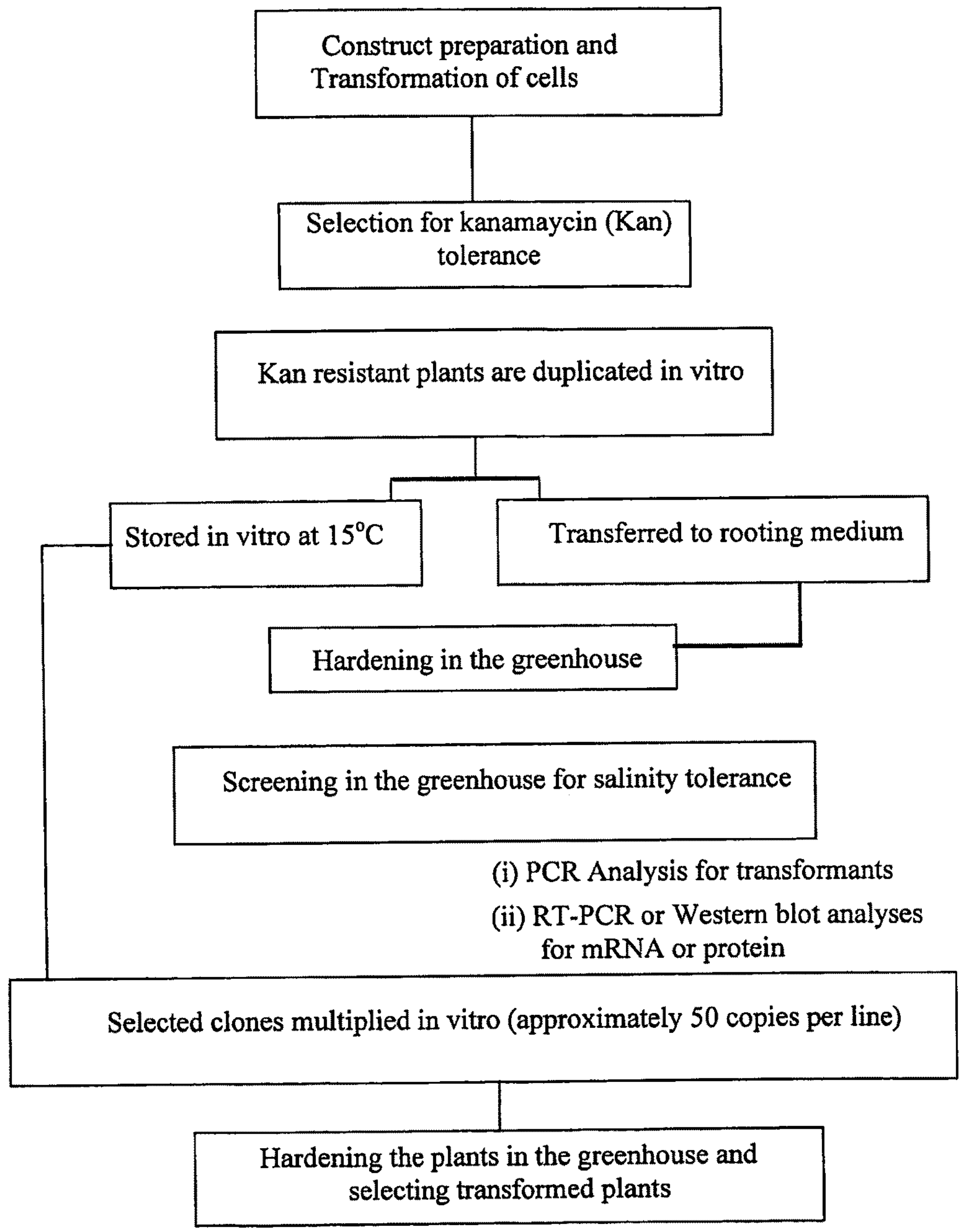
FIG. 1 illustrates schematically analysis of transgenic plants expressing candidate genes from *Dunaliella* for tolerance to high levels of NaCl

The present invention discloses transgenic plants transformed with exogenous nucleic acid encoding a *Dunaliella* plasma membrane (PM)-ATPase. The PM-ATPase is preferably a *Dunaliella* $H^+$-ATPase, a *Dunaliella* $X^+$-ATPase, or the PM-ATPase can also be a chimera of a plant PM-ATPase and a *Dunaliella* PM-ATPase. The transgenic plants of the present invention have increased tolerance to salt as compared to corresponding non-transgenic plants. The present invention also provides a method of producing a transgenic plant having an increased tolerance to salt as compared to a corresponding non-transgenic plant, a method of modifying a plant capacity to survive salt shock, and a method of modifying plant recovery after exposure to salt stress, by introducing into one or more cells of a plant exogenous nucleic acid encoding a *Dunaliella* PM-ATPase. Also provided by the present invention are plant cells comprising an exogenous nucleic acid encoding a *Dunaliella* PM-ATPase, and plant seeds and progenies obtained from the transgenic plants. The present invention also provides novel nucleic acids encoding a chimeric PM-ATPase, which comprise a first portion encoding a plant PM-ATPase or a fragment thereof, and a second portion encoding a *Dunaliella* PM-ATPase or a fragment thereof.

The present invention makes a significant contribution to the art by providing new strategies to engineer salt-tolerance in crop plants. All previous attempts rely on the over-expression of genes from plant sources. In contrast, the present invention takes advantage of the special features of the *Dunaliella* PM-ATPase which is adapted to function at very high salt concentrations, to confer salt-resistance in plants.

The present invention may be understood more readily by reference to the following detailed description of the preferred embodiments of the invention and the Examples included herein.

Definitions

The term "plant" is used herein in its broadest sense. It includes, but is not limited to, any species of woody, herbaceous, perennial or annual plant. It also refers to a plurality of plant cells that are largely differentiated into a structure that is present at any stage of a plant's development. Such structures include, but are not limited to, a root, stem, shoot, leaf, flower, petal, fruit, etc. As used herein, the term "salt" refers to any salt, such as NaCl, KCl, and/or $CaCl_2$. As used herein, "salt water" includes water characterized by the presence of salt, and preferably wherein the concentration of salt in the water is from about 0.2M to about 0.4M. In one embodiment, salt water refers to seawater.

As used herein, the term "salt-inducible" or "salt-responsive" refers to a protein or gene which is influenced by an altered environment of salt. For example, a salt-inducible or salt-responsive protein may be over-expressed or its expression may be inhibited as a result of a rise or fall in salt concentration. Alternatively, the enzymatic activity of a salt-inducible or salt-responsive protein may be altered as a response to a rise or fall in salt concentration. For example, the protein may be induced or inhibited as a result of an alteration of salt concentration. Similarly, a salt-inducible or salt-responsive gene may by up regulated or down regulated as a response to a rise or fall in salt concentration.

The term "gene" refers to a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene. The fragments may range in size from a few nucleotides to the entire gene sequence minus one nucleotide. Thus, "a nucleic acid sequence comprising at least a part of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

The term "nucleic acid" as used herein refers to RNA or DNA that is linear or branched, single or double stranded, or a hybrid thereof. The term also encompasses RNA/DNA hybrids.

An "isolated" nucleic acid molecule is one that is substantially separated from other nucleic acid molecules which are present in the natural source of the nucleic acid (i.e., sequences encoding other polypeptides). Preferably, an "isolated" nucleic acid is free of some of the sequences which naturally flank the nucleic acid (i.e., sequences located at the 5' and 3' ends of the nucleic acid) in its naturally occurring replicon. For example, a cloned nucleic acid is considered isolated. A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

The term "construct" as used herein refers to an artificially assembled or isolated nucleic acid molecule which includes the gene of interest. In general a construct may include the gene or genes of interest, a marker gene which in some cases can also be the gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

The term "vector" as used herein encompasses both expression and transformation vectors. Vectors are often recombinant molecules containing nucleic acid molecules from several sources. In a preferred embodiment of this aspect of the invention, the vector may include a regulatory element such as a promoter and an enhancer that control or influence the transcription of the gene, a nucleic acid or nucleic acid fragment according to the present invention and a terminator that direct the termination of transcription; said regulatory element, nucleic acid or nucleic acid fragment and terminator being operatively linked.

By "operatively linked", as used herein, is meant that said regulatory elements, including for example, a promoter and an enhancer, are capable of causing expression of said nucleic acid or nucleic acid fragment in a plant cell. Preferably, said regulatory element is upstream of said nucleic acid or nucleic acid fragment and said terminator is downstream of said nucleic acid or nucleic acid fragment.

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "transgenic" when used in reference to a plant or seed (i.e., a "transgenic plant" or a "transgenic seed") refers to a plant or seed that contains at least one heterologous gene in one or more of its cells. The term "transgenic plant material" refers broadly to a plant, a plant structure, a plant tissue, a plant seed or a plant cell that contains at least one heterologous gene in at least one of its cells.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

Transformation of a cell may be stable or transient. The term "transient transformation" or "transiently transformed" refers to the introduction of one or more exogenous polynucleotides into a cell in the absence of integration of the exogenous polynucleotide into the host cell's genome. Transient transformation may be detected by, for example, enzyme-linked immunosorbent assay (ELISA), which detects the presence of a polypeptide encoded by one or more of the exogenous polynucleotides. Alternatively, transient transformation may be detected by detecting the activity of the protein (e.g. β-glucuronidase) encoded by the exogenous polynucleotide. The term "transient transformant" refers to a cell which has transiently incorporated one or more exogenous polynucleotides. In contrast, the term "stable transformation" or "stably transformed" refers to the introduction and integration of one or more exogenous polynucleotides into the genome of a cell. Stable transformation of a cell may be detected by Southern blot hybridization of genomic DNA of the cell with nucleic acid sequences which are capable of binding to one or more of the exogenous polynucleotides. Alternatively, stable transformation of a cell may also be detected by enzyme activity of an integrated gene in growing tissue or by the polymerase chain reaction of genomic DNA of the cell to amplify exogenous polynucleotide sequences. The term "stable transformant" refers to a cell which has stably integrated one or more exogenous polynucleotides into the genomic or organellar DNA. It is to be understood that a plant or a plant cell transformed with the nucleic acids, constructs and/or vectors of the present invention can be transiently as well as stably transformed.

The terms "in vitro growth" or "grown in vitro" as used herein refer to regeneration and/or growth of plant material in tissue culture. Specifically, according to the present invention, a transformed plant cell or tissue is placed it in a sterile, (usually gel-based) nutrient medium, supplemented with the adequate additives to induce differentiation and plantlets growth.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "homology", as used herein, refers to a degree of sequence similarity in terms of shared amino acid or nucleotide sequences. There may be partial homology or complete homology (i.e., identity). For amino acid sequence homology amino acid similarity matrices may be used as are known in different bioinformatics programs (e.g. BLAST, FASTA, Smith Waterman). Different results may be obtained when performing a particular search with a different matrix. Degrees of homology for nucleotide sequences are based upon identity matches with penalties made for gaps or insertions required to optimize the alignment, as is well known in the art (e.g. Altschul S. F. et al., 1990, J Mol Biol 215(3):403-10; Altschul S. F. et al., 1997, Nucleic Acids Res. 25:3389-3402).

The term "variant" as used herein refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The term "fragment" as used herein refers to a polypeptide having one or more deletions of amino acid residues relative to the sequence of the native polypeptide, so long as the activity of the native polypeptide is maintained. The amino acid residues may be deleted from the amino terminus and/or carboxy terminus and/or along the peptide sequence.

Plants Transformed with Exogenous PM-ATPase

One aspect of the present invention relates to a transgenic plant transformed with exogenous nucleic acid encoding a *Dunaliella* plasma membrane (PM)-ATPase. The transgenic plant has increased tolerance to salt as compared to a corresponding non-transgenic plant. The invention is based on the discovery that transformation of tobacco plants with a nucleic acid encoding a PM-ATPase isolated from the highly salt tolerant green alga *Dunaliella*, gives rise to a transgenic plant having an increased tolerance to salt as compared to a corresponding non-transgenic plant. The salt tolerance correlates with the expression of the *Dunaliella* PM-ATPase in the transgenic plants.

The expression of a heterologous PM-ATPase in tobacco has another unexpected advantage: previous attempts to overexpress native PM-ATPases in plants have been difficult, partly due to gene silencing (Zhao R, et al., (2000) *The Plant Cell* 12:535-46). The fact that the *Dunaliella* gene differs significantly in sequence from the tobacco native enzyme, may contribute to the fact that it does not interfere with expression of the major native plant ATPase genes.

Although the invention is described and demonstrated with reference to a PM-ATPase gene isolated from *Dunaliella acidophila* or *Dunaliella salina*, and to the polypeptide products thereof, it is apparent to a person of skill in the art that the PM-ATPase source is not limited to the *Dunaliella acidophila* and *Dunaliella salina*, and that PM-ATPases isolated from other species of salt-tolerant algae in general and from *Dunaliella* in particular may be utilized as a tool to confer salt-resistance to plants. Examples of such species include but are not limited to *Dunaliella parva* and *Dunaliella bardawil*. Other algal species that can survive at high salinity and which can be utilized within the scope of the present invention include, for example *Halomonas*.

In addition, it is to be understood that although the invention is described and demonstrated with reference to a PM-$H^+$-ATPase and PM-$X^+$-ATPase, it is apparent to a person of skill in the art that other PM-ATPases can be used to confer salt resistance in plants.

The present invention also provides an isolated nucleic acid encoding a *Dunaliella* PM-ATPase or a fragment, homolog or variant thereof. In one preferred embodiment, the PM-ATPase is a *Dunaliella acidophila* $H^+$-PM-ATPase, and the nucleic acid is set forth in SEQ ID NO: 1 [GenBank and EMBL Accession No. U54690, starting at nucleotide No. 175 and ends at nucleotide No. 3638]. In another preferred embodiment, the PM-ATPase is a *Dunaliella acidophila* $H^+$-PM-ATPase, and the nucleic acid is set forth in SEQ ID NO:2 [GenBank and EMBL Accession No. U54690, starting at nucleotide No. 175 and ends at nucleotide No 3126]. In another preferred embodiment, the PM-ATPase is a *Dunaliella* salina $H^+$-PM-ATPase, and the nucleic acid is set forth in SEQ ID NO:3. In yet another preferred embodiment, PM-ATPase is a *Dunaliella salina* $X^+$-PM-ATPase, and the nucleic acid is set forth in SEQ ID NO: 6.

In yet another preferred embodiment, the PM-ATPase is a chimera of an *Arabidopsis thaliana* $H^+$-ATPase and a *Dunaliella acidophila* $H^+$-ATPase, and the nucleic acid comprises a chimera of an *Arabidopsis thaliana* $H^+$-ATPase (bases 1-2057) and a *Dunaliella acidophila* C-terminal area (bases 2058-2847) as set forth in SEQ ID NO: 4.

In yet another preferred embodiment, the PM-ATPase is a chimera of an *Arabidopsis thaliana* $H^+$-ATPase and a *Dunaliella acidophila* $H^+$-ATPase, and the nucleic acid comprises a chimera of an *Arabidopsis thaliana* $H^+$-ATPase (bases 1-2195 and 2434-3030) and a *Dunaliella acidophila* trans-membrane loop 7-8 (bases 2196-2433) as set forth in SEQ ID NO: 5.

In another aspect the present invention provides a nucleic acid encoding a PM-ATPase, comprising a first portion encoding a plant PM-ATPase or a fragment thereof, and a second portion encoding a *Dunaliella* PM-ATPase or a fragment thereof. In one embodiment, the PM-ATPase is a chimera of an *Arabidopsis thaliana* $H^+$-ATPase and a *Dunaliella acidophila* H-ATPase, and the nucleic acid comprises a chimera of an *Arabidopsis thaliana* $H^+$-ATPase (bases 1-2057) and a *Dunaliella acidophila* C-terminal area (bases 2058-2847) (SEQ ID NO: 4). In another embodiment, the PM-ATPase is a chimera of an *Arabidopsis thaliana* $H^+$-ATPase and a *Dunaliella acidophila* $H^+$-ATPase, and the nucleic acid comprises a chimera of an *Arabidopsis thaliana* $H^+$-ATPase (bases 1-2195 and 2434-3030) and a *Dunaliella acidophila* trans-membrane loop 7-8 (bases 2196-2433) (SEQ ID NO:5).

Although the chimeric genes of the present invention are exemplified by the use of the plant *Arabidopsis thaliana* $H^+$-ATPase, it is to be understood that the $H^+$-ATPase can be obtained from any other suitable plant source, for example any known *Arabidopsis* species. Similarly, the *Dunaliella* species can be any one or more of the species described above, or any other known species of *Dunaliella.*

The PM-ATPase nucleic acid can be isolated by any method known to a person of skill in the art, for example as described by Weiss et al (Weiss M & Pick U (1996) *Plant Physiol* 112:1693-1702), incorporated by reference herein. The nucleic acid encompasses any nucleic acid fragment of a PM *Dunaliella* PM-ATPase, and may be incorporated into a construct and/or a vector encoding the PM *Dunaliella*-ATPase. The PM $H^+$-ATPase nucleic acid can be incorporated into a plant transformation vector used to transform wild type plants, which is incorporated into one or more of the plant cells.

Genetic Constructs

Another aspect of the present invention relates to a construct comprising a nucleic acid encoding a *Dunaliella* PM-ATPase or a fragment, homolog or variant thereof.

Another aspect of the present invention relates to a construct comprising a nucleic acid encoding a *Dunaliella* PM-ATPase, wherein the nucleic acid comprises a polynucleotide selected from the group consisting of SEQ. ID NO:1, SEQ. ID NO:2, SEQ. ID NO:3, SEQ. ID NO:4, SEQ. ID NO:5, and SEQ. ID NO:6, and/or functionally active fragments, homologs or variants thereof.

Another aspect of the present invention relates to a vector comprising a nucleic acid encoding a *Dunaliella* PM-ATPase or a fragment, homolog or variant thereof.

Another aspect of the present invention relates to a vector comprising an isolated nucleic acid encoding a *Dunaliella* PM-ATPase wherein the nucleic acid comprises a polynucleotide selected from the group consisting SEQ. ID NO: 1, SEQ. ID NO:2, SEQ. ID NO:3, SEQ. ID NO:4, SEQ. ID NO:5, and SEQ. ID NO:6, and/or a functionally active fragment, homolog or variant thereof.

Preferably the vector is a plant transformation vector. In addition, the vector preferably further includes promoter and a terminator, wherein the promoter, nucleic acid or nucleic acid fragment and terminator being operatively linked.

The vector may be of any suitable type and may be viral or non-viral. The vector may be an expression vector. Such vectors include chromosomal, non-chromosomal and synthetic nucleic acid sequences, e.g. derivatives of plant viruses; bacterial plasmids; derivatives of the Ti plasmid from *Agrobacterium tumefaciens*, derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable, integrative or viable in the plant cell.

The regulatory element and terminator may be of any suitable type and may be endogenous to the target plant cell or may be exogenous, provided that they are functional in the target plant cell.

Preferably the regulatory element is a promoter. A variety of promoters which may be employed in the vectors of the present invention are well known to those skilled in the art. Factors influencing the choice of promoter include the desired tissue specificity of the vector, and whether constitutive or inducible expression is desired and the nature of the plant cell to be transformed (e.g. monocotyledon or dicotyledon). Particularly suitable constitutive promoters include the Cauliflower Mosaic Virus 35S (CaMV 35S) promoter and derivatives thereof, the maize Ubiquitin promoter, and the rice Actin promoter. In a currently preferred embodiment, the present invention relates to a construct wherein the PM-ATPase gene is operably linked to a 35S promoter.

A variety of terminators which may be employed in the vectors of the present invention are also well known to those skilled in the art. The terminator may be from the same gene as the promoter sequence or from a different gene.

The genetic construct of the present invention can further comprise a reporter gene or a selection marker that is effective in the target plant cells to permit the detection of transgenic cells, tissues or plants containing the genetic construct. Such selection markers and reporter genes, which are well known in the art, typically confer resistance to one or more toxins or encode for a detectable enzymatic activity, respectively. The nptII gene, whose expression results in resistance to kanamycin or hygromycin antibiotics, which are generally toxic to plant cells at a moderate concentration, can be used as a selection marker. Alternatively, the presence of the desired construct in transgenic cells may be determined by means of other techniques that are well known in the art, including PCR, Southern and Western blots.

Those skilled in the art will appreciate that the various components of the vector are operatively linked, so as to result in expression of said nucleic acid or nucleic acid fragment. Techniques for operatively linking the components of the vector of the present invention are well known to those skilled in the art. Such techniques include the use of linkers, such as synthetic linkers, for example including one or more restriction enzyme sites.

The present invention also relates to a method of producing a transgenic plant having an increased tolerance to salt as compared to a corresponding non-transgenic plant. The method comprises introducing into one or more cells of a non-transgenic plant exogenous nucleic acid encoding a *Dunaliella* PM-ATPase, thereby producing a transgenic plant having an increased tolerance to salt as compared to the corresponding non-transgenic plant.

Techniques for incorporating the *Dunaliella* PM-ATPase nucleic acid of the present invention into plant cells (for example by transduction, transfection or transformation) are well known to those skilled in the art. For example, *Agrobacterium* mediated plant transformation, particle bombardment, microparticle bombardment (e.g., U.S. Pat. No. 4,945,050; U.S. Pat. No. 5,100,792) protoplast transformation, gene transfer into pollen, injection into reproductive organs and injection into immature embryos can be used. Other techniques include electroporation to tissues, cells and protoplasts, protoplast fusion, and high velocity projectile introduction to cells, tissues, calli, immature and mature embryos. The choice of technique will depend largely on the type of plant to be transformed.

The exogenous nucleic acid can be introduced into any suitable cell(s) of the plant, such a root cell(s), stem cell(s) and/or leaf cell(s) of the plant.

In one embodiment, the construct of the present invention comprises the *Dunaliella* PM-ATPase gene operably linked to a promoter designed to over-express the PM-ATPase. In another embodiment, a construct is designed to down regulate endogenous PM-ATPase. As used herein the term "over-expression" refers to greater expression/activity than occurs in the absence of the construct. In a particular embodiment, a construct comprising a PM-ATPase gene operably linked to a chimeric promoter designed to over-express the PM-ATPase or designed to down regulate endogenous PM-ATPase is used to produce the transgenic plants of the present invention.

Any suitable plant can be used to produce the transgenic plants of the present invention. Non-limiting examples include tobacco, maize, wheat, rye, oat, triticale, rice, barley, soybean, peanut, corn, cotton, rapeseed, canola, manihot, pepper, sunflower, tagetes, Solanaceous plants, potato, eggplant, tomato, *Vicia* species, pea, alfalfa, sorghum, cucumber, lettuce, turf grass, ornamental coffee, cacao, tea, *Salix* species, oil palm coconut, perennial grass and a forage crop. A currently preferred plant is a tobacco plant or a potato plant. In addition, the transgenic plants of the present invention can be grown in any medium which supports plant growth such as soil or water (hydroponically).

As demonstrated herein, the transformed transgenic plant of the present invention expresses the polypeptide product of the PM-ATPase nucleic acid. The expression may be monitored by conventional methods known to a person skilled in the art, for example by extracting proteins from the plasma membrane of the transgenic plants and testing with antibodies directed against the *Dunaliella* PM-ATPase.

As mentioned above, the transgenic plants are highly salt-resistant, and are able to grow in a concentration of a salt that inhibits growth of a corresponding non-transgenic plant, for example a concentration of salt in the range of from about 0.1M to about 0.55M, typically at a concentration salt ranging from about 0.2M to about 0.3M.

As used herein, the term "salt" refers to any salt, such as NaCl, KCl, and/or $CaCl_2$. Thus, the present invention also provides for a method of producing a transgenic plant that grows in salt water comprising introducing into one or more cells of a plant exogenous nucleic acid encoding a *Dunaliella* PM-ATPase, thereby producing a transgenic plant which grows in salt water.

The present invention also relates to a plant cell or other plant part transformed with exogenous nucleic acid encoding a *Dunaliella* PM-ATPase.

Furthermore, also encompassed by the present invention is a plant seed transformed with exogenous nucleic acid encoding a *Dunaliella* PM-ATPase. The plant seed is advantageously used for breeding a plant having an increased tolerance to salt as compared to a corresponding plant grown from a seed produced by a corresponding non-transgenic plant. Also encompassed by the present invention are transgenic progeny of the transgenic plants described herein. Progeny transgenic plants are grown from seeds or shoots of the transgenic plants described herein.

The present invention further encompasses plants regenerated from tissue cultures obtained from the transgenic plants of the present invention. The tissue culture comprises transgenic cells or protoplasts from a tissue selected from the group consisting of, but not limited to, leaves, pollen, embryos, roots, root tips, anthers, flowers, fruit and seeds.

In a further aspect of the present invention there is provided a method of modifying plant tolerance to environmental stress and/or osmotic stress such as salt stress, by introducing into the plant a nucleic acid or nucleic acid fragment, construct and/or a vector encoding a *Dunaliella* PM-ATPase.

In a further aspect of the present invention there is provided a method of modifying plant capacity to survive salt shock, by introducing into the plant a nucleic acid or nucleic acid fragment, construct and/or a vector encoding a *Dunaliella* PM-ATPase.

The present invention thus provides novel transgenic plants which are capable of surviving and thriving in a highly saline environment. Without wishing to be bound by any particular mechanism or theory, it is proposed that the special kinetic and structural features of the *Dunaliella* PM-ATPase enzyme improve the ability of tobacco plants to maintain ionic homeostasis under salt stress. The finding that expression of a heterologous *Dunaliella* PM-ATPase gene in tobacco increases salinity tolerance suggests that PM-ATPases, especially PM-$H^+$-ATPases and PM-$X^+$-ATPases, are limiting elements for survival under salt stress in plants. The reason for this is not clear, since PM-ATPases energize diverse processes in plants in different tissues, including turgor maintenance, ionic homeostasis and uptake of metabolites and minerals, all of which may contribute to salinity tolerance. A possible function may be to energize $Na^+$ elimination and/or $Na^+$ xylem loading in roots. Since $Na^+$ extrusion via $Na^+/H^+$ antiporters is driven by the proton motive force across the plasma membrane, which is generated by the PM $H^+$-ATPase, it is conceivable that a major function of these enzymes under salt stress is to energize elimination of $Na^+$ ions that enter root cells either out of the root or loading them into the xylem for compartmentalization in leaves. Additional functions may be maintenance of a large membrane potential to enhance $K^+$ accumulation in order to avoid loss of turgor and/or to energize the uptake of essential metabolites and mineral whose availability decreases in saline soil.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Salinity Tolerance in Tobacco Plants Expressing *D. acidophila* PM $H^+$-ATPase DNA Constructs Two constructs of the DAHA (*D. acidophila* PM $H^+$-ATPase): A) the intact gene (SEQ. ID NO:1, FIG. 2); and B) a C-truncated version lacking the 120 last amino acids coding region (SEQ. ID NO:2, FIG. 3), were prepared by incorporation of Not1 restriction sites through polymerase chain reaction to nucleotides 175 and 3638 of DAHA gene (to obtain intact *D. acidophila* PM $H^+$-ATPase) or to nucleotides 175 and 3126 of DAHA gene (to obtain the C-truncated *D. acidophila* PM H-ATPase).

The deletion of the C-terminal domain, which functions as an auto-inhibitory domain in higher plants and in *Dunaliella* (Palmgren M G (2001) supra; Sekler I & Pick U (1993) supra), is expected to enhance the activity of the expressed enzyme, as demonstrated previously by expression of a C-truncated AHA-2 ATPase from *A. thaliana* in yeast.

Transformation Constructs and Vectors

The genes were cloned into the plant transformation vector, introduced into *Agrobacterium* strain LBA4404, and used to transform wild type Tobacco plants as described below. Transformed plants were selected in vitro for kanamycin resistance. About 200 transgenic tobacco plants were developed from each construct. Kanamycin-resistant plants were duplicated in vitro, stored at 15° C., transferred to rooting medium and taken for hardening in greenhouse as described in FIG. 1.

Tobacco Transformation

Fully expanded young leaves were used as explants for transformation. Leaf segments were disinfected by immersion in a 0.5% solution of mercuric chloride ($HgCl_1$) for 15 minutes followed by 20 minutes immersion in 1.1% sodium hypochloride and rinsed twice with distilled sterile water. The leaf blade was divided and subsequently cut into 1×1 cm segments. The leaf segments were wounded in transverse incisions with a sterile blade. The leaf segments were co-incubated for 30 min. in 2YT medium containing 100 μM acetosyringone and approximately $10^7$ cells per ml of *Agrobacterium tumefaciens* strain LBA4404 harboring the appropriate plasmid. Following co-incubation the segments were blotted onto a piece of Whatmann No 48) filter paper and placed in 9 cm diameter Petri dishes containing RMTT-1041 medium containing: MS salts (macro and micro elements), 0.1 mg/l IAA, 2 mg/l zeatin, 1% (W/V) manitol, 2% (WV) sucrose and 0.65% agar. After 48 hrs the segments were transferred to Petri dishes containing fresh RMTT-1041 supplemented with 300 mg/l Cefotaxime antibiotic and 50 mg/l kanamycin (RMTT-1041B). After one week the segments were transferred to a fresh medium as above with no Cefataxime (RMTT-1041C). Cali started to appear 4 weeks after co-cultivation. The cali were transferred to incrementing concentrations of kanamycin (in intervals of 50 mg/l higher concentration each transfer) every 3-4 weeks, up to 500 mg/l). After approximately 3 months plants were regenerated from the cali. Plantlets were rooted on MS medium supplemented with 500 mg/l of kanamycin. Rooted plants that did not show chlorotic regions on the leaves were taken to acclimatization in a glass-covered greenhouse.

Characterization of Transgenic Tobacco Plants

Screening Transgenic Plants Grown in the Greenhouse for Salinity Tolerance

FIG. 4 shows a picture of salt-resistant and control tobacco plants cultivated with or without salt. FIG. 4A shows control plant grown without salt (left) and transformed plants grown in the presence of 250 mM NaCl (right). FIG. 4B shows control plant (left) and transgenic plant transformed with *D. acidophila* PM $H^+$-ATPase (SEQ. ID NO:1) (right) grown in the presence of 250 mM NaCl. The results show that control plants are unable to grow in the presence of salt (250 mM NaCl), whereas the transformed plants exhibit salt-resistant properties in the presence of this salt concentration.

Expression of PM $H^+$-ATPase Protein in Tobacco Plants

In order to examine the expression of *D. acidophila* PM $H^+$-ATPase protein in transgenic tobacco plants, proteins were extracted from plasma membrane preparation of tobacco leaves and roots, and tested by Western analysis using antibodies directed against the *D. acidophila* $H^+$-ATPase.

Plasma membrane preparation was preformed essentially as previously described (Katz A, et al., (1986) *FEBS Lett.* 202:141-144), with minor modifications (Zchut et al., (2003) *J Plant Physiol* 160:185-192). Protein extraction was performed as described below.

As shown in FIG. 5, the antibodies cross-reacted with protein components of about 100 kDa in the preparations obtained from transgenic plants, but not with proteins extracted from control plants. The results demonstrate that only the salt-resistant transgenic tobacco plants express the algal protein. Thus, these results clearly indicate that expression of the *D. acidophila* PM $H^+$-ATPase confer salt-resistant properties to the transformed tobacco plants.

Example 2

Salinity Tolerance in Potato Plants Expressing *D. salina* PM $H^+$-ATPase

An $H^+$-ATPase gene from *Dunaliella* salina (SEQ. ID NO:3, FIG. 6) was constructed into Ti plasmid and transformed into potato leaves of the cultivar "Desiree". After selection for tolerance to kanamycin, plantlets regenerated from the transformed leaves were transferred to tubes for rooting and growth. The resulted transgenic plants were hardened in a glass-covered greenhouse. A total of 120 plants representing 36 independent transgenic lines were hardened. Other clones of the same lines were stored in vitro (146 plantlets). Selection of plants tolerant to salinity was performed as detailed in FIG. 1. After selection for tolerance to kanamycin, plantlets were transferred to tubes for rooting and growth as described in Example 1. Other transgenic plants were hardened in a glass-covered greenhouse. Several clones were hardened, and other clones of the same line were stored in vitro (FIG. 1).

Plantlets were planted in pots with Perlite only and acclimatized in a greenhouse with 93% humidity, moderate temperature (21-31° C.) and 20% shade. After several weeks the plantlets were moved to another greenhouse with droplets-irrigation, 70% humidity and 14-28° C.

Testing for Tolerance to Salinity:

Tolerance to salinity was tested in-vitro and with hardened plants in the green house.

1. In Vitro Experiment 50 transgenic plants were planted in tubes containing growth medium with 150 mM NaCl. As a control—50 transgenic plants were planted on the appropriate growth medium, and 5 non-transgenic plants were also planted on salted medium as a negative control. After 4 weeks 10 clones of transgenic potato plants remained unaffected by the salt. (FIG. 7)

Expression of PM $H^+$-ATPase Protein in Tobacco Plants

Proteins from the 10 clones that remained unaffected by salt, as well as from two of the control plants (transgenic but apparently sensitive to salt), and from WT "Desiree" (non-transgenic plant), were tested by Western blot analysis.

Protein extraction was performed in cold 4% SDS buffer containing 200 mM Tris-HCl pH 7.5, 4 mM EDTA, 2 mM PMSF, 10% B mercaptoethanol and 20% glycine. Leaf samples from transgenic plants were ground in liquid nitrogen in a mortar and pestle and subsequently centrifuged at 12,000 rpm for 20 min. The supernatant was used for separation on a 15% SDS-PAGE gel electrophoresis using BioRad modular mini-gel apparatus. The proteins were blotted onto a nitrocellulose paper and Western analysis was performed using a standard procedure. The blots were incubated first with a polyclonal primary antibody at a concentration of 1:500 for each antibody and subsequently with a secondary goat anti rabbit cross-linked to alkaline phosphatase (BioRad USA) at a concentration of 1:3000. Results are shown in FIG. 8.

Figure 8:
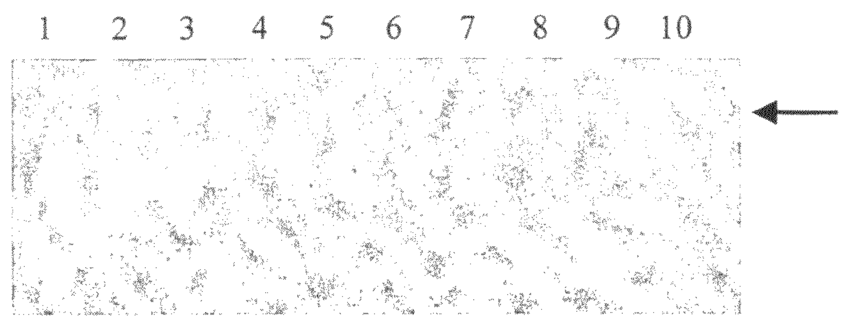
FIG. 8 is a Western blot analysis of recombinant $H^+$ATPase from *D. salina* in transgenic potato plants. Lane 1: Molecular size marker, lane 2, 3 transformed lines that did not resist the selection marker, lane 4: non-transgenic line, lanes 5-10: transgenic lines. The arrow points to a band of approximately 105 K Daltons postulated to be the recombinant $H^+$ ATPase.

From FIG. 8 it is evident that the transgenic plants express the *D. salina* $H^+$-ATPase protein in potato plants. The blots show two bands that were clearly separated in the transgenic plants, while in the non-transgenic plants neither band appeared. The appearance of the second unexpected band (of approximately 100 kilo-Daltons) is unclear; although it is postulated that this is due to post-translational processing of the recombinant protein in the plant cells.

2) Greenhouse Experiment (Environmental Conditions are as Mentioned Above):

10 clones of transgenic plantlets and 10 plantlets of non-transgenic lines (all from "Desiree") were gradually exposed to elevated concentrations of salt, of 50, 100 and 150 mM NaCl that was added to the irrigation solution. The plants were watered manually with ¼ concentration of Hoagland solution (basic solution) containing 50 mM NaCl for 3 days, and then with the Hoagland solution only for the rest of the week. The subsequent week the plants were watered for 3 days with the basic solution containing 100 mM NaCl, followed by 3 days of basic solution only. In the following week the salt concentration was raised to 150 mM. Three transgenic plants (No. 256, 279 and 289) tolerated these concentrations of salt better then the other clones.

Example 3

Cloning of aha-2/*D. Acidophila* $H^+$-ATPase Chimeras

Expression of Plasma Membrane $H^+$-ATPases in Plants

Figure 9:
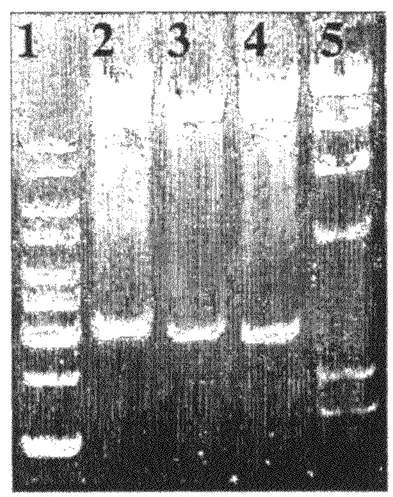
FIG. 9 shows agarose gel with $H^+$-ATPase constructs in plant transformation vector #288. Lane 1: 1 Kb ladder (Fermentas) Top band: 10 Kb Low band: 1.5 Kb. Lane 2: *Arabidopsis thaliana* $H^+$-ATPase (aha-2). Lane 3: Chimera of *Arabidopsis thaliana* $H^+$-ATPase (aha-2) (bases 1-2057) with the *Dunaliella acidophila* C-terminal area (bases 2058-2847). Lane 4: *Arabidopsis thaliana* $H^+$-ATPase (aha-2) (bases 1-2195 and 2434-3030) including *Dunaliella acidophila* trans-membrane loop 7-8 (bases 2196-2433). Lane 5: %-HindIII ladder (MBI) Top band: 24 Kb 2 Kb.
Figure 10:
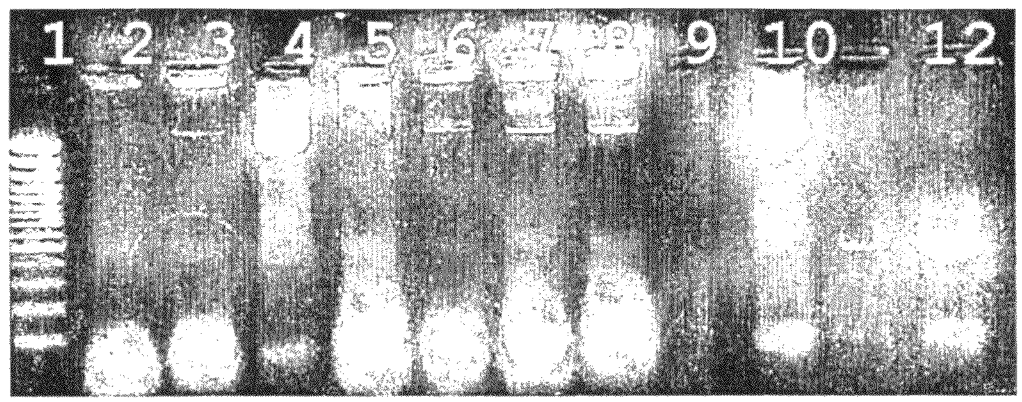
FIG. 10 shows an agarose gel with *Agrobacterium* clones of $H^+$-ATPase constructs in plant transformation vector #288. Lane 1: 100 bp ladder (Fermentas) Top band: 3 Kb Low band: 0.1 Kb. Lane 2, 3: *Arabidopsis thaliana* $H^+$-ATPase (aha-2) in *Agrobacterium* clones 3, 4. Lane 4: *Arabidopsis thaliana* $H^+$-ATPase (aha-2) in *E. Coli* (control). Lane 5-8: Chimera of *Arabidopsis thaliana* $H^+$-ATPase (aha-2) (bases 1-2057) with the *Dunaliella acidophila* C-terminal area (bases 2058-2847) in *Agrobacterium* clones 1-4. Lane 10: Chimera of *Arabidopsis thaliana* ATPase (aha-2) (bases 1-2057) with the *Dunaliella acidophila* C-terminal area (bases 2058-2847) in *E. Coli* (control). Lane 12: #288 Ti-plasmid in *E. Coli* (control).

The plasma membrane $H^+$-ATPase involved in salinity tolerance from *Arabidopsis thaliana*, cloned into the plant transformation vector #288 (aha-2, FIG. 9), was introduced into *Agrobacterium* strain LBA4404 (FIG. 10). Tobacco wild type plants (SR1) were transformed with these *Agrobacteria*. Transformed plants were selected in vitro on kanamycin containing media. Selected transgenic plants were evaluated for enhanced salinity tolerance. FIG. 9 depicts $H^+$-ATPase constructs in plant transformation vector #288. Lane 1: 1 Kb ladder (Fermentas) Top band: 10 Kb Low band: 1.5 Kb. Lane 2: *Arabidopsis thaliana* $H^+$-ATPase (aha-2). Lane 3: Chimera of *Arabidopsis thaliana* H-ATPase (aha-2) (bases 1-2057) with the *Dunaliella Acidophila* C-terminal area (bases 2058-2847). Lane 4: *Arabidopsis thaliana* $H^+$-ATPase (aha-2) (bases 1-2195 and 2434-3030) including *Dunaliella acidophila* trans-membrane loop 7-8 (bases 2196-2433). Lane 5: λ-HindIII ladder (MBI) Top band: 24 Kb 2 Kb.

Chimeric Genes:

*Dunaliella acidophila* plasma membrane $H^+$-ATPases that are adapted to function at high salinity or at acidic pH show exceptional high activity in tobacco plants and are more effective than the homologues proton-ATPases from plants under stress conditions. The potential of the *Dunaliella* plasma membrane $H^+$-ATPases to enhance salinity tolerance is thought to be induced by the C-terminal area of the protein. A chimera of the 5' area (first 2057 bases) of $H^+$-ATPase gene from *Arabidopsis thaliana* with the *Dunaliella acidophila* C-terminal area (bases 2058-2847) was constructed in a Ti-plasmid (SEQ. ID NO:4—FIG. 11). The chimera Ti-plasmid construct was introduced into the LBA4404 *Agrobacterium* strain and transformed into tobacco plants. FIG. 10 depicts *Agrobacterium* clones of $H^+$-ATPase constructs in plant transformation vector #288. Lane 1: 100 bp ladder (Fermentas) Top band: 3 Kb Low band: 0.1 Kb. Lane 2, 3: Two clones of *Arabidopsis thaliana* $H^+$-ATPase (aha-2) in *Agrobacterium* (designated clones 3 and 4). Lane 4: *Arabidopsis thaliana* $H^+$-ATPase (aha-2) in *E. Coli* (control). Lane 5-8: Chimera of *Arabidopsis thaliana* $H^+$-ATPase (aha-2) (bases 1-2057) with the *Dunaliella acidophila* C-terminal area (bases 2058-2847) in four *Agrobacterium* clones (clones 1-4). Lane 10: Chimera of *Arabidopsis thaliana* H-ATPase (aha-2) (bases 1-2057) with the *Dunaliella acidophila* C-terminal area (bases 2058-2847) in *E. Coli* (control). Lane 12: #288 Ti-plasmid in *E. Coli* (control)

Figure 13:
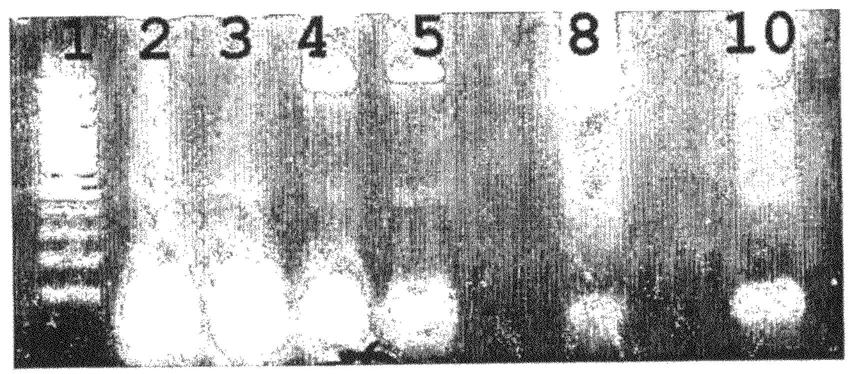
FIG. 13 shows an agarose gel with *Agrobacterium* chimeric clones of $H^+$-ATPase constructs in plant transformation vector #288. Lane 1: 100 bp ladder (Fermentas) Top band: 3 Kb Low band: 0.1 Kb. Lanes 2-5: *Arabidopsis thaliana* $H^+$-ATPase (aha-2) (bases 1-2195 and 2434-3030) including *Dunaliella acidophila* trans-membrane loop 7-8 (bases 2196-2433) in *Agrobacterium* clones 1-4. Lane 8: *Arabidopsis thaliana* $H^+$-ATPase (aha-2) (bases 1-2195 and 2434-3030) including *Dunaliella acidophila* trans-membrane loop 7-8 (bases 2196-2433) in *E. Coli* (control). Lane 10: $H_2O$ (control).

The proton-ATPase molecule from *Dunaliella acidophila* has a trans-membrane loop that is thought to play a role in enhancing salinity tolerance. A plant transformation vector harboring the *Arabidopsis thaliana* $H^+$-ATPase into which the *Dunaliella Acidophila* trans-membrane loop 7-8 (bases 2196-2433) (SEQ. ID NO:5—FIG. 12) was inserted by electroporation into the LBA4404 *Agrobacterium* strain and transformed into tobacco wild type plants. FIG. 13 depicts *Agrobacterium* chimeric clones of $H^+$-ATPase constructs in plant transformation vector #288. Lane 1: 100 bp ladder (Fermentas) Top band: 3 Kb Low band: 0.1 Kb. Lanes 2-5: *Arabidopsis thaliana* $H^+$-ATPase (aha-2) (bases 1-2195 and 2434-3030) including *Dunaliella Acidophila* trans-membrane loop 7-8 (bases 2196-2433) in *Agrobacterium* clones 1-4. Lane 8: *Arabidopsis thaliana* $H^+$-ATPase (aha-2) (bases 1-2195 and 2434-3030) including *Dunaliella Acidophila* trans-membrane loop 7-8 (bases 2196-2433) in *E. Coli* (control). Lane 10: $H_2O$ (control).

Example 4

Cloning of *D. salina* $X^+$-ATPase

The $X^+$-ATPase from *D. salina* (SEQ. ID NO: 6, FIG. 14) was constructed in a Ti plasmid inserted by electroporation into the LBA4404 *Agrobacterium* strain as described in Examples 1-3. As described in the previous examples, this construct can be used to transform tobacco plants in order to confer salt resistance. Using this construct, transgenic plants partially resistant to salt were constructed.

It will be appreciated by a person skilled in the art that the present invention is not limited by what has been particularly shown and described hereinabove. Rather, the scope of the invention is defined by the claims which follow.

The invention claimed is:

1. A transgenic plant having an increased tolerance to salt as compared to a corresponding non-transgenic plant, wherein the transgenic plant is transformed with an exogenous nucleic acid encoding a *Dunaliella* plasma membrane (PM) ATPase, said nucleic acid consisting of SEQ ID NO:2.

2. The transgenic plant according to claim 1, wherein the PM-ATPase nucleic acid is present in a plant transformation vector.

3. The transgenic plant according to claim 1, wherein said plant grows in a concentration of a salt that inhibits growth of a corresponding non-transgenic plant.

4. The transgenic plant according to claim 3, wherein the concentration of salt is from about 0.1M to about 0.55M.

5. The transgenic plant according to claim 1, wherein said plant is selected from the group consisting of a tobacco plant and a potato plant.

6. A plant seed produced by the transgenic plant according to claim 1, wherein said seed comprises said exogenous nucleic acid.

7. A tissue culture comprising at least one plant cell or protoplast transformed with an exogenous nucleic acid encoding a *Dunaliella* plasma membrane (PM)-ATPase, said nucleic acid consisting of SEQ ID NO: 2, the plant cell or protoplast having an increased tolerance to salt as compared to a cell of a corresponding cell or protoplast of a non-transgenic plant.

8. The tissue culture according to claim 7, wherein the at least one plant cell or protoplast is obtained from a plant part selected from the group consisting of leaves, pollen, embryos, roots, root tips, anthers, flowers, fruit and seeds.

9. A plant regenerated from the tissue culture according to claim 7.

10. A plant cell transformed with an exogenous nucleic acid encoding a *Dunaliella* plasma membrane (PM)-ATPase, said nucleic acid consisting of SEQ ID NO: 2, the plant cell having an increased tolerance to salt as compared to a cell of a corresponding non-transgenic plant.

11. The plant cell according to claim 10, wherein said plant cell grows in a concentration of a salt that inhibits growth of a corresponding non-transgenic plant cell.

12. The plant cell according to claim 11, wherein the concentration of salt is from about 0.1M to about 0.55M.

13. The plant cell according to claim 10, wherein said plant cell is selected from the group consisting of a tobacco plant cell and a potato plant cell.

14. A method of producing a transgenic plant having an increased tolerance to salt as compared to a corresponding non-transgenic plant, comprising:

a. transforming at least one plant cell with an exogenous nucleic acid encoding a *Dunaliella* plasma membrane (PM)-ATPase as set forth in SEQ ID NO: 1 or SEQ ID NO: 2;

b. regenerating the transformed cell into a plant having an increased tolerance to salt as compared to the corresponding non-transgenic plant;

c. growing the transgenic plant in a concentration of salt from about 0.1M to about 0.55M.

15. The method according to claim 14, wherein the PM-ATPase nucleic acid is present in a plant transformation vector.

16. The method according to claim 14, wherein the plant is selected form the group consisting of a tobacco plant and a potato plant.

17. The method according to claim 14, further comprising generating a seed from said transgenic plant, wherein said seed comprises said exogenous nucleic acid.

* * * * *

SEQUENCE LISTING

```
<160> NUMBER OF SEQ ID NOS: 6

<210> SEQ ID NO 1
<211> LENGTH: 3464
<212> TYPE: DNA
<213> ORGANISM: Dunaliella acidophila

<400> SEQUENCE: 1

aggatgagtg gaaaggagag gaccgaggaa aatggggccg tcaagcagga cacgaaggag      60

caggtcaaga aatcggccga caatggagat aaaggcgtgg acgaggtgga cttcgccaag     120

attgggctgg aggatgcctt caagtacctg aattgctccg agcatggtct gagcggcgct     180
```

```
gaagccgaag cacggcttaa acagcacggg cctaataagc tccctgacaa ctcccgtaac    240
ccagttctgg tgtactttgg gtacatgtgg aaccccttgg cttgggccat ggaggcggct    300
gctatcattg ccattgcttt ggtggatggt gcagacttcg cgctgattgt gggcctgctg    360
atcatcaatg ccactatcag tttcgtcgag gagagcaatg ctgataaggc tatcaaggcc    420
ttgtcagctg ccctagcacc caaggccatg gccttacgaa atggagccat ggtgaccata    480
gacgcggtgg accttgtgcc cggggatgtg attttgattc ggatcggtaa cgttgtgccc    540
gccgatgtta aattgcttcc ggaacatggc gcggatgact atgagacgcc cgtgcagatt    600
gaccaagctg ccttgacagg agagtcctta ccagccaaga agttcacagg caacgtggcc    660
ttcagcggtt ctactgtcaa acaaggagag cgacacgctg ttgtgtatgc caccggcgtg    720
aacaccttct ttggccgtgc tgctgcgctc atcagtggga ctcacaacgt agcaaatatt    780
cagcgtgtca tgaacaggat cggtggcctt tgtctcatca ccattggagt atgggtcgtc    840
attgaagtgc ctgtgcagtt tgcacattat aagcattcat gcgtagctgg caaagagggc    900
tgccccaccc tactcaacat gctggttata ctggtgggtg ctattcccat cgccatgccc    960
actgtgctgt cagtgacctt ggccctggga gcttacaagc ttgcacgtga aggcgctatt   1020
gtgactcgga tgagtgctgt ggaagagatg gcaggcttgg atgtgttatg ctctgacaag   1080
actggaacct tgacccttaa caagctatca atcgatccta gcaatgtgtt ccctgtgggc   1140
acgatggaca tcccagaggt tatgaagttc ggcgctttgt ctgccaacat aatcactgag   1200
gagcctatcg atatggtgct gtgggagtca taccctgagc gggagaaatt aaaatcagag   1260
tacaagcaca ccaagtactt cccattcaac cccaatgaca agatcaccat cgcaaccgtc   1320
cttgagattg ccactggccg cgtgttccga gtcctcaaag gctcccctca ggtggtcttg   1380
gccaaggcat ggaatgcgca agccctggat gggcctgtga atgaaaagat aaaagagtat   1440
gcaggcagag gcttccgttc tctgggcatt gccatggcag agggggatgg caaggacgga   1500
acaaagtggg agatgctggc ggtgctgccc atgtttgacc cccctcgcca cgacaccaag   1560
gaaaccattg agcgctgcat gaagcagggt attgcagtca agatggtcac aggcgaccac   1620
ttgctgattg gtaaagagac tgccaagatg ctgggcatgg gtactgagat gtaccccagt   1680
gaggtgctga tcaaggcccg caatggtgat gtggaggcgc cgcatggtta caaaaactac   1740
gtggcaatgg tggaggcatg caacggcttt gcacaggtct tccctgaaca caagtttgaa   1800
attgtcgaaa tcctgcaaga agcccaccac cgtgttggca tgacaggtga cggtgtgaac   1860
gacgcgcctg cgctcaagaa ggcgcatgta ggtgtggctg tggcagatgc cacagatgcc   1920
gcccgaggtg ccgctgacat cgtgctcacc gagcctggtc tatcaaccat tgtgaccgct   1980
gtcattggcg cacgcaagat cttcaagcgc atgaccactt atgccaagta caccatttcc   2040
gtgaccttcc gtatcgcctt taccttcggc ctcctcactg tcatctacga ctggtacttc   2100
cccaccatcc tcatcgtcat cttggctgtc tttaatgatg gtgccatgat cgccctatcc   2160
aaggaccgtg tggtggcctc tgtgttgcct agcacctgga acctcgccac catcttcgta   2220
ccgggttttg tctacgcaat gtggctgact ctctcctcct gggcactgta ccaggtggcc   2280
acacatagca ccttctttga acgcatgacc ccactgccat cactgaacac ccagcatgcg   2340
actctcatat cctggtgtga ggatgagatc agcagcaagt tgggcgtcaa tcctcaagat   2400
tccctgtgca cgtatccaag ctatgctgat cagctgaatg aatgcaaagg ctctgtgagc   2460
ctgagctcac aggtccctgg cgtgcccacc attttggatc agtgcgtaac tgagcagcgc   2520
tacattcgag atgccttgac acgtgccctc atttacaccc acctctctgt ctctggccaa   2580
```

```
gccgttgtgt ttgtggtgcg cacgtccggc ttctctctga aggaagtggc aggcgtctcc   2640

acctatgtcg ctttcgctct tgcccagttt ggtgccacaa tgtttggcat ctttggcctg   2700

ggaggctata acaagccccg acagaatttt gacaactgcc agttctgtga ttactccacc   2760

cataatcgcg tgctgttctt taactcagag gtggaacctc gcgctggtac agaatctgtc   2820

tacactgctt ctgtcattgg atgcggaggt tatgtcattg tcgcttggat ctgggctgct   2880

ctgttctaca ctgcgctgga tcccttgaag tggggcttga tgtggatcat gaacgatgat   2940

ggcttcaggg accggcacgc ctggcgcaag tccaaccacg aggccatgga gcgccgtagc   3000

agggagcagt tggacaacaa agagttcgct ggcccctcag gcatggtgcc tgccaacttc   3060

tctaaccctc ttggccgtgc ctccatgtcc aagcccgtgt ccgctttgct tgaccgaaag   3120

tctgcatccc ttgtggctat taaccgcagc tccatgactg tcagtcacga ccccaaccat   3180

gcactgaaca tcggacgccg ctccatgatt ggacgcccct ctggtccttt gggacgcaac   3240

tccaacacgg gtcaaagcaa ccccctgaac agctcttcag tggagatcaa gcccgatgcg   3300

cccaacaagg tgtaagaaaa cccatcagtg agatgtaagg caaactactg tgcaagaggc   3360

gatgtcggta catgcgctcg tgtgtctgtg taggaaggtc gtgcgagtgc cctatgtcat   3420

gggccctatt tcaatgtttt ctatgtacaa gaacttgagt ggta                    3464
```

<210> SEQ ID NO 2
<211> LENGTH: 2946
<212> TYPE: DNA
<213> ORGANISM: Dunaliella acidophila

<400> SEQUENCE: 2

```
aggatgagtg gaaaggagag gaccgaggaa aatggggccg tcaagcagga cacgaaggag     60

caggtcaaga aatcggccga caatggagat aaaggcgtgg acgaggtgga cttcgccaag    120

attgggctgg aggatgcctt caagtacctg aattgctccg agcatggtct gagcggcgct    180

gaagccgaag cacggcttaa acagcacggg cctaataagc tccctgacaa ctcccgtaac    240

ccagttctgg tgtactttgg gtacatgtgg aacccccttgg cttgggccat ggaggcggct   300

gctatcattg ccattgcttt ggtggatggt gcagacttcg cgctgattgt gggcctgctg    360

atcatcaatg ccactatcag tttcgtcgag gagagcaatg ctgataaggc tatcaaggcc    420

ttgtcagctg ccctagcacc caaggccatg gccttacgaa atggagccat ggtgaccata    480

gacgcggtgg accttgtgcc cggggatgtg attttgattc ggatcggtaa cgttgtgccc    540

gccgatgtta aattgcttcc ggaacatggc gcggatgact atgagacgcc cgtgcagatt    600

gaccaagctg ccttgacagg agagtcctta ccagccaaga agttcacagg caacgtggcc    660

ttcagcggtt ctactgtcaa acaaggagag cgacacgctg ttgtgtatgc caccggcgtg    720

aacaccttct ttggccgtgc tgctgcgctc atcagtggga ctcacaacgt agcaaatatt    780

cagcgtgtca tgaacaggat cggtggcctt tgtctcatca ccattggagt atgggtcgtc    840

attgaagtgc ctgtgcagtt tgcacattat aagcattcat gcgtagctgg caaagagggc    900

tgccccaccc tactcaacat gctggttata ctggtgggtg ctattcccat cgccatgccc    960

actgtgctgt cagtgacctt ggccctggga gcttacaagc ttgcacgtga aggcgctatt   1020

gtgactcgga tgagtgctgt ggaagagatg gcaggcttgg atgtgttatg ctctgacaag   1080

actggaacct tgacccttaa caagctatca atcgatccta gcaatgtgtt ccctgtgggc   1140

acgatggaca tcccagaggt tatgaagttc ggcgctttgt ctgccaacat aatcactgag   1200
```

```
gagcctatcg atatggtgct gtgggagtca taccctgagc gggagaaatt aaaatcagag   1260

tacaagcaca ccaagtactt cccattcaac cccaatgaca agatcaccat cgcaaccgtc   1320

cttgagattg ccactggccg cgtgttccga gtcctcaaag gctcccctca ggtggtcttg   1380

gccaaggcat ggaatgcgca agccctggat gggcctgtga atgaaaagat aaaagagtat   1440

gcaggcagag gcttccgttc tctgggcatt gccatggcag agggggatgg caaggacgga   1500

acaaagtggg agatgctggc ggtgctgccc atgtttgacc cccctcgcca cgacaccaag   1560

gaaaccattg agcgctgcat gaagcagggt attgcagtca agatggtcac aggcgaccac   1620

ttgctgattg gtaaagagac tgccaagatg ctgggcatgg gtactgagat gtaccccagt   1680

gaggtgctga tcaaggcccg caatggtgat gtggaggcgc cgcatggtta caaaaactac   1740

gtggcaatgg tggaggcatg caacggcttt gcacaggtct tccctgaaca caagtttgaa   1800

attgtcgaaa tcctgcaaga agcccaccac cgtgttggca tgacaggtga cggtgtgaac   1860

gacgcgcctg cgctcaagaa ggcgcatgta ggtgtggctg tggcagatgc cacagatgcc   1920

gcccgaggtg ccgctgacat cgtgctcacc gagcctggtc tatcaaccat tgtgaccgct   1980

gtcattggcg cacgcaagat cttcaagcgc atgaccactt atgccaagta caccatttcc   2040

gtgaccttcc gtatcgcctt taccttcggc ctcctcactg tcatctacga ctggtacttc   2100

cccaccatcc tcatcgtcat cttggctgtc tttaatgatg gtgccatgat cgccctatcc   2160

aaggaccgtg tggtggcctc tgtgttgcct agcacctgga acctcgccac catcttcgta   2220

ccgggttttg tctacgcaat gtggctgact ctctcctcct gggcactgta ccaggtggcc   2280

acacatagca ccttctttga acgcatgacc ccactgccat cactgaacac ccagcatgcg   2340

actctcatat cctggtgtga ggatgagatc agcagcaagt tggcgtcaa tcctcaagat    2400

tccctgtgca cgtatccaag ctatgctgat cagctgaatg aatgcaaagg ctctgtgagc   2460

ctgagctcac aggtccctgg cgtgcccacc attttggatc agtgcgtaac tgagcagcgc   2520

tacattcgag atgccttgac acgtgccctc atttacaccc acctctctgt ctctggccaa   2580

gccgttgtgt ttgtggtgcg cacgtccggc ttctctctga aggaagtggc aggcgtctcc   2640

acctatgtcg ctttcgctct tgcccagttt ggtgccacaa tgtttggcat ctttggcctg   2700

ggaggctata acaagccccg acagaatttt gacaactgcc agttctgtga ttactccacc   2760

cataatcgcg tgctgttctt taactcagag gtggaacctc gcgctggtac agaatctgtc   2820

tacactgctt ctgtcattgg atgcggaggt tatgtcattg tcgcttggat ctgggctgct   2880

ctgttctaca ctgcgctgga tcccttgaag tggggcttga tgtggatcat gaacgatgat   2940

ggcttc                                                              2946
```

<210> SEQ ID NO 3
<211> LENGTH: 4863
<212> TYPE: DNA
<213> ORGANISM: Dunaliella salina

<400> SEQUENCE: 3

```
tgcaggattc ggcacgaggg agtggtgggc ttgcttcctg gctccagagt agttccgcac     60

ctgttcacga gcaaatggcg cacctgtgag gcccgctgcg tgcaagtgcg ccttcttcgc    120

gccacactcc cacctttgac acgcagacac agagcgccct gacctgtcag agcttgcttt    180

aggccgtgag ctgccaaccg actcagccgt ctctgcctgg agagggcccc tgggcccgct    240

gagtgccgca acatggcgga catcaaggaa ggagtcgagg aaggatcggt gaaggtggac    300

atgatcaagg agcccctcac acaaggggac actggcgtgg atgaggtgga ctttgccaag    360
```

-continued

```
attactctgg acgatgcctt caagtacttg aattgcaaca agcacgggct cagcagtgcc    420
gaagcagctg ctcgtcttca acagcacggg cccaacaagc ttcctgacag ttcacgcaac    480
cctgtccttg tcttccttgg atacatgtgg aaccccctgg cgtgggccat ggaggcagcc    540
gcaatcatct ccattgccct cctggatgtg gcagatttcg tgctcattgt gggcttgctg    600
ctcatcaatg ccattatcag tttctatgag gagagcaacg ccgacaaggc catcaaggcc    660
ttgacagctg cccttgcacc caaggccatg gtcgtgcgag atggtgccat tgtgaccatc    720
gatgctgtga atctcgtgcc gggggacgtc atcttaatcc gcttgggcaa catcgtacca    780
gcagacgtca agctgctgga agaagaggga gctgatgagg gggagcagga agcgcccatg    840
cagatcgacc aagccgccct cacaggagag tcccttccgg ccaagaagtt cacgggcgac    900
gtggccttca gcggctcgag catcaagcag ggagagcgcc atgcagtggt gtatgctact    960
ggtgtgaaca ccttcttcgg acgtgcagct gccctcatca gcggcaccaa caacgtatcc   1020
aacctgcaga ctgtcatgaa caagatgagc gccatctgca tcgtcaccat cctgctgtgg   1080
gtcgttgtcg agctggccgt gcaatttggg cactactcgc atgaatgcgt tggtggcaga   1140
gagggctgcc ccaccctgct gaatatgctg gtggtgctgg tgggcggtat tcccattgcc   1200
atgcccactg tgctgtccgt gaccctcgcc ctgggtgcct acaagcttgc acgcgagggt   1260
gccatcgtca cccgtatgag cgccgtagag gagatggcag gcatggatgt gctgtgctct   1320
gacaaaaccg gcaccctcac cttgaacaag ctgtccattg acaagagcat ggtggtgccg   1380
gtgggcaaca tgggcgtgga tgagatcatg agaatgggcg gcctgtctgc cattacagtc   1440
acagaggagc ccatcgatat ggtgctgtgg gagtcttatc cagacaggga aacaattaag   1500
agggactaca agcacaccaa gtacttcccc ttcatcccca atgacaagat taccatcgca   1560
acgtgcctgg agatcgccac cggtagggtg ttccgcgtgc tgaagggctc tcctcaggtg   1620
gtgctggcca aggcgtggaa tgcagccgag ctggatgcca ccgtgaacca gaagatggtg   1680
gaatttgcaa accgcggctt ccgcgcgctg ggcttggcta tggcagacgg cgacggcaaa   1740
gatggcacca agtgggagat gctggcgctg ctgccgctgt ttgacccccc tcgccacgac   1800
accaaggaga ccatcgagca ctgccagaac cagggcatcc aagtcaagat gatcactggt   1860
gaccacttgc ttatcgggaa ggaaaccgcc aagatgctgg gcatgggcac tgagatgttc   1920
cccagtgagg tcatgatcaa ggcccgcaat ggcgacgcaa gccagctgca cggctacaag   1980
aactttgtgg agatggtgga gacctgcaac ggctttgccc aggtgttccc ggagcacaag   2040
tttgagatcg tcaagatcct gcaggactcc aaccacgtcg tcggcatgac aggtgatggt   2100
gtgaatgacg cacccgccct gaagaaggct gacgtgggtg tggctgtggc tgacgccacc   2160
gatgctgctc gtggtgctgc cgacatcgtg ctgacggagc ctggcttgtc caccatcgtg   2220
acggcggtga tcggcgcgcg caagatcttc cagcgcatga ccacctactc caagtacacc   2280
atcgccatga ccttccgtat ctgcttcacc tttgggctga tcaccgtcat ctacgactgg   2340
tacttcccca ccatcctcat cgtcatcatg ggtgtcttca acgatggtgc catgattgcg   2400
ctgtctaagg accgtgtggt ggcctccaag acgcccaata gctggaacat caccaacatc   2460
ttcatcatgg gcatggtgta cggcctgtac ctcaccctct ccacatgggc cttgtaccag   2520
actgccacca agaccacgtt cttcgaggac aagacaccct tgcattcact caatgaccag   2580
tacagcgtcc tgcagccctg gtgtgaggac gaagtgcggg ccaagcttgg acaaaccatc   2640
gacccctacg cctcactgtg cgagtccaac agctacgcca agcagtttga cgagtgcgag   2700
```

```
ggataccaga agggctcagg cgtgcaggtg gaggacgtcc ctaccctgca tgcccaatgc   2760
gtgactgagc aacgttacct gcgtggcgcc atgacgcgct ccctcatcta cacccaggtc   2820
tcaatttctg gtcaggccct cgtgtttgtc gtccgtactg cgggctactc cttgatggag   2880
cgcgcgggca cctccacata cctggccttc ttctttgccc aggtgggcgc cacgctgttt   2940
ggtatctttg gcctgggtgg ctttgagaag ccccgccacc agctggagga ctgccagttc   3000
tgcgactact ccttccatga gcccgtagac tggtttgact ccgggattgt gcctgagtcc   3060
ggcacagagt ccgacttcac tgcctctgtc atcggatgcg gtggttacgt gattgtggcc   3120
tggatctggt ctgccatttg gtacgtgctg ctggacccca tcaagtggat cctgttctgg   3180
atcttgaacg aggagggctt cagggacacg atgtcctggc gcgagagcac caagaggagc   3240
ctggaccgcc gcagcaagga tgacatcggc gacaaggagt tcacggggcc ctctggcatg   3300
gtgccggcca actactccaa cccccctgggc cgtgcgtcca tgtccaagcc tgtgtcagct   3360
gtgctggacc gcaagtccgc ctccctggtt gctatcaacc gcaactctat gactgtgagc   3420
caggacccca accgcgcgct caacatcggc cggcgctcca tgattggccg cccctctggg   3480
cctgttggcc gcacgtccat gcccttgggc cgtatctcgc gcacttccaa caccttgtcc   3540
acaggctcta aggatggcca gatcggcaga ggaagcaagc ctctgaacag ctcgtccgct   3600
gagatcaagc ccgacaagta tgacttcgct tccaccatca gggagtgagc cctctctctc   3660
tcgtcagcaa gctgtcaaaa gctgttgaga gtgattgggt gacccccatg aatggataat   3720
ggagagtgca tgtgaaacct ttggttccag caagcagggg cagaacaccc ttgccttagt   3780
tcgaacaaac tggccatcag ggttgatcct cctgtgcagg tagagggcgc gtccttcagc   3840
gctccactcc ttgtctgagt gcacatacgt gcgtgcctgc acctgttctc acccattctc   3900
cctcattgtt gcaatgtgga agtattgctg tgctcatatg atgattcact tttcaacagc   3960
tagggagcag ctaggcgcaa tgtgtgcgct cttttagcaa ggctgctagg tcagtgaaca   4020
acaactaggg agcagcttgg ggcgctaagt gcgcactgat gggcaaagct gctcaatcag   4080
tgaacgtatg ctagagaatt taaatacccg cagttcgcag gattatgcac ctctccgtgt   4140
gtcctgcaag tgtgggcatg cgcagcactt tgcagggata tgctcttctg tgtgtgtttt   4200
gcaagtgtgg gcttgcgcac ccatgctcca cagatatccg tgtgtggcga agaggttggt   4260
ggacatgctt tcatagttgc gacttgtttc atgcttttga aggggagcaa gccaaagttt   4320
tagcaatgct gctgcatatg tctctggatt gtgtagaggc taccttattc tgccatccgc   4380
ttcctctaga gcatgtgctt acctcttgtg taaggagttc ttgctactga ttacctcggt   4440
gaggctttgc tcgcgtgtgc tcgcatgctc acaggtgcgg ctattacgca atgttgcctg   4500
cattttgctt ctttatccca attcctttgt gtcttctctg gtgcttttct gtgacgcaag   4560
ctttccacct taattgttct tgcggctcaa cacaactgca tgcatgagtg agacatgcat   4620
ccagaaagac gcagaaccca ggaatttgtg ttaggataac ttacttatga agcctttacc   4680
ggtattaata caggtattag gtaaatcagc gtgatcagct tgtggaacac gtatgactat   4740
tatgtgttgc atcgttctga tgagtatttt catcattgat gcaccctttt tggtattcat   4800
tgctgggatt tgcgtgattt ggtattcatt attccttgta acagagtgag cataatgaaa   4860
aaa                                                                 4863
```

<210> SEQ ID NO 4
<211> LENGTH: 2874
<212> TYPE: DNA
<213> ORGANISM: Artificial sequence
<220> FEATURE:
<223> OTHER INFORMATION: A chimera of H+-ATPase genes from Arabidopsis thaliana and Dunaliella Acidophila

<400> SEQUENCE: 4

```
atgtcgagtc tcgaagatat caagaacgag actgttgatc tggaaaaaat tccgattgag     60
gaagttttcc agcagctaaa atgttcaagg gaaggattga caacgcagga aggggaggac    120
aggattcaga tctttggccc caacaagctc gaagagaaaa aggaaagcaa acttctgaag    180
tttttggggt ttatgtggaa tccactttca tgggtcatgg aaatggctgc aatcatggcc    240
attgctttgg ccaacggtga tggtaggcct ccggattggc aggattttgt tggtattatc    300
tgtctgttgg ttatcaactc taccatcagt tttatcgaag aaaacaatgc tggtaatgct    360
gctgctgctc ttatggctgg tcttgctcct aaaaccaagg ttcttaggga tggaaagtgg    420
agtgaacaag aagctgctat tcttgtccca ggagatattg ttagcattaa attaggagac    480
attatcccag ctgatgcccg tctacttgaa ggtgatcctt taaaggttga ccaatctgct    540
ctaactggag agtcccttcc tgtaaccaag cacccgggtc aagaagtttt ctctggttca    600
acctgcaaac aaggagaaat cgaggcggtt gttattgcca ctggggttca taccttcttc    660
ggtaaagctg ctcaccttgt ggacagcact aaccaagttg gacatttcca gaaggttctt    720
acagccattg ggaacttctg tatctgttcc attgctatcg gtatggtgat tgagatcatc    780
gtcatgtatc cgatccaacg ccgaaagtac agagatggaa ttgacaacct tttggtcctc    840
ttgatcggtg gtatccccat tgctatgcct acagtcttgt ccgtgaccat ggctattggg    900
tctcacaggt tgtctcagca aggtgccatc accaagcgta tgactgccat tgaagagatg    960
gcaggaatgg atgtcctgtg cagtgacaaa accgggacac taaccctcaa caaattgagt   1020
gtggacaaaa acttggtcga ggttttctgc aagggtgtgg agaaagatca agtcctatta   1080
tttgcagcta tggcttccag ggttgagaac caggatgcca ttgatgcagc catggttggg   1140
atgcttgctg atccaaagga ggctagagct ggaatcaggg aagttcactt ccttccattc   1200
aaccctgtgg ataagagaac tgctttgact tacattgacg gcagtggtaa ctggcacaga   1260
gtcagtaaag gtgctcctga gcagatcctc gaacttgcca aagccagcaa tgatcttagc   1320
aagaaggtgc tctccattat tgacaagtat gctgagcgtg gtcttaggtc gttggctgtt   1380
gctcgccagg tggtgccaga gaaaacaaag gaaagcccag gtgcgccatg ggaatttgtt   1440
ggcttgttgc cactttttga tcccccaaga catgacagtg ctgaaacaat tcgacgggct   1500
ttgaatcttg gtgttaacgt caagatgatc actggtgacc aacttgctat tggtaaggaa   1560
actggtcgca gacttggaat gggaacaaac atgtatccat cttcggctct tcttggtaca   1620
cacaaagacg caaacctcgc atccattcct gttgaggagt tgattgaaaa ggctgatgga   1680
tttgccggag tcttcccaga gcacaaatac gaaattgtga aaaagttgca ggagaggaag   1740
catattgttg gaatgactgg tgatggtgtc aatgatgccc ctgctctaaa gaaagctgat   1800
atcggtattg ctgttgctga tgctacagat gctgctcgtg gtgcttcaga tatcgtgctc   1860
actgagcctg gactcagcgt tattatcagt gctgttctca ccagcagagc tattttccag   1920
agaatgaaga actatactat ctatgcagtc tcaatcacca tccgtattgt gtttggtttc   1980
atgcttattg ctttgatatg ggaatttgac ttctcagcct tcatggttct gatcattgcc   2040
attcttaacg acggtaccat gatcgcccta tccaaggacc gtgtggtggc ctctgtgttg   2100
cctagcacct ggaacctcgc caccatcttc gtaccgggtt ttgtctacgc aatgtggctg   2160
actctctcct cctggacact gtaccaggtg gccacacata gcaccttctt tgaacgcatg   2220
```

```
accccactgc catcactgaa cacccagcat gcgactctca tatcctggtg tgaggatgag   2280

atcagcagca agttgggcgt caatcctcaa gattccctgt gcacgtatcc aagctatgct   2340

gatcagctga atgaatgcaa aggctctgtg agcctgagct cacaggtccc tggcgtgccc   2400

accattttgg atcagtgcgt aactgagcag cgctacattc gagatgcctt gacacgtgcc   2460

ctcatttaca cccacctctc tgtctctggc caagccgttg tgtttgtggt gcgcacgtcc   2520

ggcttctctc tgaaggaagt ggcaggcgtc tccacctatg tcgctttcgc tcttgcccag   2580

tttggtgcca caatgtttgg catctttggc ctgggaggct ataacaagcc ccgacagaat   2640

tttgacaact gccagttctg tgattactcc acccataatc gcgtgctgtt ctttaactca   2700

gaggtggtgc ctcgcgctgg tacagaatct gtctacactg cttctgtcat tggatgcgga   2760

ggttatgtca ttgtcgcttg gatctgggct gctctgttct acactgcgct ggatcccttg   2820

aagtggggct tgatgtggat catgaacgat gatggcttca gggactaaac tagt         2874
```

<210> SEQ ID NO 5
<211> LENGTH: 3030
<212> TYPE: DNA
<213> ORGANISM: Artificial sequence
<220> FEATURE:
<223> OTHER INFORMATION: A chimera of H+-ATPase genes from Arabidopsis thaliana and Dunaliella Acidophila

<400> SEQUENCE: 5

```
atgtcgagtc tcgaagatat caagaacgag actgttgatc tggaaaaaat tccgattgag     60

gaagttttcc agcagctaaa atgttcaagg gaaggattga caacgcagga aggggaggac    120

aggattcaga tctttggccc caacaagctc gaagagaaaa aggaaagcaa acttctgaag    180

tttttggggt ttatgtggaa tccactttca tgggtcatgg aaatggctgc aatcatggcc    240

attgctttgg ccaacggtga tggtaggcct ccggattggc aggattttgt tggtattatc    300

tgtctgttgg ttatcaactc taccatcagt tttatcgaag aaaacaatgc tggtaatgct    360

gctgctgctc ttatggctgg tcttgctcct aaaaccaagg ttcttaggga tggaaagtgg    420

agtgaacaag aagctgctat tcttgtccca ggagatattg ttagcattaa attaggagac    480

attatcccag ctgatgcccg tctacttgaa ggtgatcctt taaaggttga ccaatctgct    540

ctaactggag agtcccttcc tgtaaccaag cacccgggtc aagaagtttt ctctggttca    600

acctgcaaac aaggagaaat cgaggcggtt gttattgcca ctggggttca taccttcttc    660

ggtaaagctg ctcaccttgt ggacagcact aaccaagttg gacatttcca gaaggttctt    720

acagccattg ggaacttctg tatctgttcc attgctatcg gtatggtgat tgagatcatc    780

gtcatgtatc cgatccaacg ccgaaagtac agagatggaa ttgacaacct tttggtcctc    840

ttgatcggtg gtatccccat tgctatgcct acagtcttgt ccgtgaccat ggctattggg    900

tctcacaggt tgtctcagca aggtgccatc accaagcgta tgactgccat tgaagagatg    960

gcaggaatgg atgtcctgtg cagtgacaaa accgggacac taaccctcaa caaattgagt   1020

gtggacaaaa acttggtcga ggttttctgc aagggtgtgg agaaagatca agtcctatta   1080

tttgcagcta tggcttccag ggttgagaac caggatgcca ttgatgcagc catggttggg   1140

atgcttgctg atccaaagga ggctagagct ggaatcaggg aagttcactt ccttccattc   1200

aaccctgtgg ataagagaac tgctttgact tacattgacg gcagtggtaa ctggcacaga   1260

gtcagtaaag gtgctcctga gcagatcctc gaacttgcca aagccagcaa tgatcttagc   1320

aagaaggtgc tctccattat tgacaagtat gctgagcgtg gtcttaggtc gttggctgtt   1380
```

```
gctcgccagg tggtgccaga gaaaacaaag gaaagcccag gtgcgccatg ggaatttgtt   1440

ggcttgttgc cactttttga tcccccaaga catgacagtg ctgaaacaat tcgacgggct   1500

ttgaatcttg gtgttaacgt caagatgatc actggtgacc aacttgctat tggtaaggaa   1560

actggtcgca gacttggaat gggaacaaac atgtatccat cttcggctct tcttggtaca   1620

cacaaagacg caaacctcgc atccattcct gttgaggagt tgattgaaaa ggctgatgga   1680

tttgccggag tcttcccaga gcacaaatac gaaattgtga aaagttgca ggagaggaag   1740

catattgttg gaatgactgg tgatggtgtc aatgatgccc ctgctctaaa gaaagctgat   1800

atcggtattg ctgttgctga tgctacagat gctgctcgtg gtgcttcaga tatcgtgctc   1860

actgagcctg gactcagcgt tattatcagt gctgttctca ccagcagagc tattttccag   1920

agaatgaaga actatactat ctatgcagtc tcaatcacca tccgtattgt gtttggtttc   1980

atgcttattg ctttgatatg ggaatttgac ttctcagcct tcatggttct gatcattgcc   2040

attcttaacg acggtaccat catgacaatc tcaaaggaca gagttaagcc atctcccaca   2100

cctgatagct ggaaacttaa agaaattttt gctactggag tcgttctagg aggctaccag   2160

gccatcatga ctgttatttt cttctgggcg gcgcaccata gcaccttctt tgaacgcatg   2220

accccactgc catcactgaa cacccagcat gcgactctca tatcctggtg tgaggatgag   2280

atcagcagca agttgggcgt caatcctcaa gattccctgt gcacgtatcc aagctatgct   2340

gatcagctga atgaatgcaa aggctctgtg agcctgagct cacaggtccc tggcgtgccc   2400

accattttgg atcagtgcgt aactgagcag cgccacgagc taatgggtgc ggtgtactta   2460

caagttagta tcattagtca agctctgatc ttcgtcacaa gatcaaggag ttggtctttt   2520

gttgaacgtc ctggagcatt gctgatgatt gctttcctca ttgcacaact gattgctact   2580

ttgattgcgg tttacgccaa ctgggaattt gcaaagatta ggggtattgg atggggatgg   2640

gctggtgtga tctggctata cagtattgtc acatacttcc cattggacgt tttcaagttt   2700

gccattcgat acatcttgag cggaaaggcg tggctcaact tgtttgagaa caagacggct   2760

ttcacgatga agaaagatta cggaaaagaa gagagagagg ctcaatgggc acttgctcaa   2820

aggacacttc acggtttaca gccaaaagaa gctgttaaca tcttccctga gaaaggaagt   2880

tacagagaat tgtctgagat cgctgagcaa gctaagagaa gagctgagat cgctaggctt   2940

agggagctgc acacactcaa gggacatgtg gaatcagtcg tgaagctaaa gggcttggac   3000

attgaaactc ccagtcacta cactgtgtag                                   3030
```

```
<210> SEQ ID NO 6
<211> LENGTH: 4138
<212> TYPE: DNA
<213> ORGANISM: Dunaliella salina

<400> SEQUENCE: 6

agcccgaagg cggctgtttg agctaggagt cactaggatt attggccggg cgaacacagg     60

aaagacaggc agcagcagca tctgcggaca ctcactgcct ttttgcagcc cagacctgca    120

cgaacgacaa gggagacagc cccgccagag cagcaggctc aaatgggcct gaccattgag    180

ccccccccatg atcacggact gacaacccag gaggttgagc agctgcagaa ggagtggggt    240

ctcaaccatg tcgctgccaa gacgatcccg gagtggaaga aaatccttga tcgctacctg    300

gactgggtgt cgctcatcat tctcatttcc gccatcattt ccgcggcggt gcccgtcaat    360

ggcgaccagg gctggacctc ctttgtgatg ctcatcctcg agctgcagtt cgtggtgtgg    420
```

```
atgggctact actcggaccg gaatgcggga gatgccgtcg ctgagcttgc ggccctgtct    480
gcacccatgt gccactgctt gcggaacggg aagtggggca gcctgccggt gaaggagctg    540
gtgcctggcg acatcattgg cctcaagggt ggtgatgtca tcccagcaga cagtaagctc    600
attggagagg gagagcccct gaagattgat gagtcctcac tgacagggga gtgccttgca    660
gtcacgaggc accctggcca agagattctt gcgggtgctg tggtggtgtc tggtgagctg    720
gacgccatgg tcactgctac tggtgtgaac tccttctttg gtaagacaat ggccttgctg    780
gccgtccccc ccgagcgtgg acacttgcag caggtgctca accgtgtgtc cattgccctg    840
gccctgtttg ccgtcgctgg ctgcgccatc attctgggtg tgctcaccgg tcactacgac    900
aaccccccctg ggtattccat cgtcactgtc ttcgtcattt tcacctccgt ggtgcccatt    960
ggcatgcctg tggtcaccac cactgtgctg gctgtgggtg cccgggagat ggcccgcgag   1020
aaggccattg tcacaaggct gtcagccctg gaagagatgt ctggtatgga ggtgctggct   1080
tccgataaga ctggcactct cacccttaac cagctgagcc ttgacaagga ggacatcctg   1140
aactggggta cccataccaa ggatgatgtg ctgctttact cctgcctgag tgccaaatgg   1200
gagaacaatg atgccatcga taaagccgtg accaactccc tgggagacaa gaagtatgtt   1260
gccggctaca agatcaccaa gttcagcccc ttcaaccccg tggacaagaa gaccaccgcc   1320
cacaccatca cccccactgg cgagaagctg atcaccacca agggtgcccc ccagatcatt   1380
ggtgacatgc tggctgaccc tgctgcacgc caggcctgcg cagactacat tgcagagcgc   1440
gcctcccgcg gcctgcgctc cctgggtgtt gcccgctccg atgatgatgg ccagacctgg   1500
tccctggtgg gcctcatctc cttgctggac ccccctcgcc ctgactctgg agagaccatc   1560
aagctggccc agtccatggg tgtggcagtg aagatggtga caggcgacca gtttgccatt   1620
gccgtggaga cctgcaagcg cctgggcatg ggctctacca tcatggaggg caagacggtc   1680
atggcaggcc tgaagggcgg cgatgagggc aagcctgacc ctgtcctgat ccagcactgc   1740
gacgagagtg atggctttgc cggcgtgtac ccggagcaca agcacatgat tgtgtcagca   1800
ttgcaggcca aggggcgcct ggttggtatg acaggtgatg gtgtgaacga tgctcccgcc   1860
ctgaagaagg ccaacgtcgg tattgccgtc gctggtgcca catctgctgc caagggtgct   1920
gcagatatca tcctgaccag ggagggtatc agcaccatca tcattgccat cgtgcgctcc   1980
cgcaagatct tccgccgcct ggagatgtac atcatctacc gcatggcctc ctccgtgctc   2040
atcctgggct tcttcttctt tgccatcctc atctttgact tcgagatccc cacctggatc   2100
ctggtgctga tttccatgct caacgacgcc tccgtcattg ccacctccta cgacgcggtg   2160
cacagctctg actacccccct gcactggaac atgaccaagg atctggcgat tgccttctcc   2220
attgccatgg tgggcattgt gggcaacgtg ctgctggtgc ccttcgtccg ccctgatctg   2280
tggtttgagt ggcctgagct tgacaccgag cctgcgctca agaccccccc tgacaatggc   2340
gtgtccacct ctggcaagga gtcggccctg atcttcctgt ccctctccgg catggtccag   2400
ctgaacatca tcctgacccg caacccctcc ttctggtggc acttcagcaa gaagagcgcc   2460
cccaagccgt cccccatctt gctggtccct gtgacatgct tcctgggtgg ttccaccttc   2520
atgtccgtgt actggaacgg caacatcaag cctgacggac agcgctacct gtttgagggc   2580
gcaggctggc acgcggtgct gctggtgtgg ccctatgttt tcgtcttctg ggtcatcgct   2640
gacttcttca aggtggccat cagctccgtc ttcgtgaagg ccgacctgat caaggatgag   2700
ctcaagggcc acattgatgg taaggagaag acccccggct gggtcaaggc cctggactgg   2760
cctggtgaga ccgccgacaa gatcagtgac aagattgagg cctgcttcga cggcatgtgc   2820
```

-continued

```
tcttgctttg agaagaaaga gaagaaggcc aagttccagc gcacgtccgt cgtgtctgag   2880

aaggagggag agggccaggt gcatgtgcaa gtggagggtg agaagcaggc ctaatcaagc   2940

cctacgggtc atgggcctgc tcatgcagtg agcgcatgct cagctgcagg tacgtcacgc   3000

agcatgagcc acaatccgaa tgtctgctcg tgtggtttgg aaggggaagg caggcgcacg   3060

atggaggggg gttgccagct tacatttttg tctcgagtgc gcctcttttg cttggttgta   3120

gagtgacttg gtggttgagg cagacggagg gcctcccatc gatcaatccc acacgattct   3180

cttttactgt gcgttaaagt tttgccaaac taggccgtac acacctgccc gctcacgcca   3240

ttttgtttgg cttcctggca atgagttgta gcctgtgagc gcatttaaaa gtactgcata   3300

tgcactgttg tgctatagga tctaaaacaa caatggaggc gtgcgtgtct gtagtttgtc   3360

gtggaggcac gtgctcatgc atgcaattgt cctggtgcct caggcctcct cccctccttg   3420

tatgaaagat tgctttttag cttagcgtct gatttatggc ggtggaggag gagacaacat   3480

agcagcagaa gtttctacgg tgttgtggcg tgtgctcatc cgttagcatt ctacagttgc   3540

cacgctaggt tgctgcctcc gggcatgttc cagttggtcc tctcagattg catgatgcaa   3600

tttccgtctg aaagcatgcg tgagggcaca tttctgcccc tggcatacat acatgtagct   3660

gtcttccaca gtggatgggt aggtagttcc ggaatgggcg ggcacgcgcc atgaccagct   3720

gggtccacta gggtcaggag atgcccagtc ccgatatcct tccattttgc gacgcatgaa   3780

acacatcctg agtgtcggct tagcaggagt gtgttccagg agcaagctcc agcttgcttt   3840

atgaggcagg ggaatgggtg tcaatgccca gcgcgtgccc ttcctgaagg caggggctgg   3900

ccggcatgcc tatagtatgt actttaattt ccgtatgatt tgttcagcag gctgtgtgtt   3960

tgctcgataa actctcattt tattgcggtc atttggacct gtttctacac tcaaaaccta   4020

actttcaact ctatagggtg ttggttttta cacttcggtt gtgcacgaga aaggtagcct   4080

ggttttcagt ggggcgctgt aagtgtacac agtttcaaaa aaaaaaaaaa aaaaaaa      4138
```